US011986442B2

(12) United States Patent
Hagras et al.

(10) Patent No.: US 11,986,442 B2
(45) Date of Patent: May 21, 2024

(54) INHIBITION OF RESPIRATORY COMPLEX III BY LIGANDS THAT INTERACT WITH A REGULATORY SWITCH

(71) Applicant: The Regents of the University of California, Oakland, CA (US)

(72) Inventors: Muhammad Hagras, Davis, CA (US); Alexei Stuchebrukhov, Davis, CA (US)

(73) Assignee: The Regents of the University of California, Oakland, CA (US)

( * ) Notice: Subject to any disclaimer, the term of this patent is extended or adjusted under 35 U.S.C. 154(b) by 239 days.

(21) Appl. No.: 17/339,620

(22) Filed: Jun. 4, 2021

(65) Prior Publication Data

US 2021/0309617 A1    Oct. 7, 2021

Related U.S. Application Data

(60) Division of application No. 16/531,511, filed on Aug. 5, 2019, now Pat. No. 11,058,645, which is a continuation of application No. PCT/US2018/017638, filed on Feb. 9, 2018.

(60) Provisional application No. 62/457,684, filed on Feb. 10, 2017.

(51) Int. Cl.

| | |
|---|---|
| *A61K 31/047* | (2006.01) |
| *A61K 31/05* | (2006.01) |
| *A61K 31/09* | (2006.01) |
| *A61K 31/12* | (2006.01) |
| *A61K 31/122* | (2006.01) |
| *A61K 31/192* | (2006.01) |
| *A61K 31/196* | (2006.01) |
| *A61K 31/351* | (2006.01) |
| *A61K 31/353* | (2006.01) |
| *A61K 31/404* | (2006.01) |
| *A61K 31/416* | (2006.01) |
| *A61K 31/5513* | (2006.01) |
| *A61P 35/00* | (2006.01) |
| *C07C 35/42* | (2006.01) |
| *C07C 43/295* | (2006.01) |
| *C07C 49/577* | (2006.01) |
| *C07C 205/45* | (2006.01) |
| *C07C 271/58* | (2006.01) |
| *C07C 317/44* | (2006.01) |
| *C07D 243/24* | (2006.01) |
| *C07D 309/14* | (2006.01) |
| *C07D 407/04* | (2006.01) |
| *C07D 493/04* | (2006.01) |

(52) U.S. Cl.
CPC ............ *A61K 31/047* (2013.01); *A61K 31/05* (2013.01); *A61K 31/09* (2013.01); *A61K 31/12* (2013.01); *A61K 31/122* (2013.01); *A61K 31/192* (2013.01); *A61K 31/196* (2013.01); *A61K 31/351* (2013.01); *A61K 31/353* (2013.01); *A61K 31/404* (2013.01); *A61K 31/416* (2013.01); *A61K 31/5513* (2013.01); *A61P 35/00* (2018.01); *C07C 35/42* (2013.01); *C07C 43/295* (2013.01); *C07C 49/577* (2013.01); *C07C 205/45* (2013.01); *C07C 271/58* (2013.01); *C07C 317/44* (2013.01); *C07D 243/24* (2013.01); *C07D 309/14* (2013.01); *C07D 407/04* (2013.01); *C07D 493/04* (2013.01)

(58) Field of Classification Search
CPC .................................................. A61K 31/047
See application file for complete search history.

(56) References Cited

U.S. PATENT DOCUMENTS

| | | | |
|---|---|---|---|
| 6,281,212 B1 | 8/2001 | Schwender et al. | |
| 8,815,844 B2 | 8/2014 | Clement et al. | |
| 2005/0019766 A1 | 1/2005 | Feng et al. | |
| 2005/0256308 A1 | 11/2005 | Watanabe et al. | |
| 2008/0280294 A1 | 11/2008 | Petros et al. | |
| 2011/0144192 A1 | 6/2011 | Dudley | |

FOREIGN PATENT DOCUMENTS

WO    2018/148554 A1    8/2018

OTHER PUBLICATIONS

Hagras et al. Journal of Physical Chemistry B, 2016, 120(10): 2701-2708.*
Adam-Vizi et al., Bioenergetics and the Formation of Mitochondrial Reactive Oxygen Species, Trends in Pharmacological Sciences, vol. 27, No. 12, Dec. 2006, pp. 639-645.
Baker et al., Protein Structure Prediction and Structural Genomics, Science, vol. 294, Oct. 5, 2001, pp. 93-96.
Borchart et al., Isolation and Amino Acid Sequence of the 9.5 KDa Protein of Beef Heart Ubiquinol: Cytochrome C Reductase, FEBS Lett., vol. 200, No. 1, May 5, 1986, pp. 81-86.
Caricato et al., Gaussian 09 IOps Reference, Jul. 2013, 170 pages.
Dallakyan et al., Small-Molecule Library Screening by Docking with PyRx, Methods in Molecular Biology, vol. 1263, Jan. 2015, 12 pages.
Forli et al., Computational Protein-Ligand Docking and Virtual Drug Screening with the Autodock Suite, Nat. Protoc., vol. 11, No. 5, May 2016, 30 pages.
Fruehauf et al., Reactive Oxygen Species: A Breath of Life or Death?, Clin. Cancer Res., vol. 13, No. 3, Feb. 1, 2007, pp. 789-794.
Hagras et al., Internal Switches Modulating Electron Tunneling Currents in Respiratory Complex III, Biochimica et Biophysica Acta, vol. 1857, No. 6, Jun. 2016, pp. 749-758.
Hagras et al., Novel Inhibitors for a Novel Binding Site in Respiratory Complex III, The Journal of Physical Chemistry B, vol. 120, No. 10, Mar. 17, 2016, pp. 2701-2708.

(Continued)

*Primary Examiner* — Rei Tsang Shiao
(74) *Attorney, Agent, or Firm* — Kilpatrick Townsend & Stockton LLP

(57) ABSTRACT

The present invention provides methods for inhibiting respiratory complex III in a cell. The present invention also provides methods for treating cancer in a subject.

16 Claims, 14 Drawing Sheets

(56) References Cited

OTHER PUBLICATIONS

Hagras et al., Transition Flux Formula for the Electronic Coupling Matrix Element, The Journal of Physical Chemistry B, vol. 119, No. 24, Mar. 2015, pp. 7712-7721.

Hayashi et al., Electron Tunneling in Respiratory Complex I, PNAS, vol. 107, No. 45, Nov. 9, 2010, pp. 19157-19162.

Irwin et al., ZINC—A Free Database of Commercially Available Compounds for Virtual Screening, J. Chem. Inf. Model., vol. 45, No. 1, Jan.-Feb. 2005, pp. 177-182.

Iwata et al., Complete Structure of the 11-Subunit Bovine Mitochondrial Cytochrome bc1 Complex, Science, vol. 281, No. 5373, Jul. 3, 1998, pp. 64-71.

Jiang et al., Cytochrome C-Mediated Apoptosis, Annu Rev Biochem., vol. 73, 2004, pp. 87-106.

Kawanishi et al., Structure-Based Drug Design of a Highly Potent CDK1,2,4,6 Inhibitor with Novel Macrocyclic Quinoxalin-2-One Structure, Bioorganic & Medicinal Chemistry Letters, vol. 16, No. 19, Oct. 1, 2006, pp. 5122-5126.

Klauda et al., Update of the Charmm All-Atom Additive Force Field for Lipids: Validation on Six Lipid Types, J. Phys. Chem. B, vol. 114, No. 23, Jun. 17, 2010, pp. 7830-7843.

Kumari et al., g_mmpbsa-A GROMACS Tool for High-Throughput MM-PBSA Calculations, Journal of Chemical Information and Modeling, vol. 54, No. 7, Jul. 28, 2014, pp. 1951-1962.

Lenaz, The Mitochondrial Production of Reactive Oxygen Species: Mechanisms and Implications in Human Pathology, IUBMB Life, vol. 52, Nos. 3-5, Sep.-Nov. 2001, pp. 159-164.

Mitchell, Chemiosmotic Coupling in Oxidative and Photosynthetic Phosphorylation, Biochim Biophys Acta., vol. 1807, No. 12, Dec. 2011, pp. 445-501.

Mitchell, Coupling of Phosphorylation to Electron and Hydrogen Transfer by a Chemi-Osmotic Type of Mechanism, Nature, vol. 191, Jul. 8, 1961, pp. 144-148.

Stuchebrukhov, Long-Distance Electron Tunneling in Proteins, Theoretical Chemistry Accounts, vol. 110, 2003, pp. 291-306.

Stuchebrukhov, Toward AB Initio Theory of Long-Distance Electron Tunneling in Proteins: Tunneling Currents Approach, Advances in Chemical Physics, vol. 118, Mar. 2007, pp. 1-44.

Stuchebrukhov, Tunneling Currents in Long-Distance Electron Transfer Reactions. III. Many-Electron Formulation, The Journal of Chemical Physics, vol. 108, No. 20, May 22, 1998, pp. 8499-8509.

Stuchebrukhov, Tunneling Currents in Long-Distance Electron Transfer Reactions. V. Effective One Electron Approximation, The Journal of Chemical Physics, vol. 118, No. 17, May 1, 2003, pp. 7898-7906.

Sugioka et al., Mechanism of 02- Generation in Reduction and Oxidation Cycle of Ubiquinones in a Model of Mitochondrial Electron Transport Systems, Biochimica et Biophysica Acta, vol. 936, No. 3, Dec. 7, 1988, pp. 377-385.

Szatrowski et al., Production of Large Amounts of Hydrogen Peroxide by Human Tumor Cells1, Cancer Research, vol. 51, No. 3, Feb. 1, 1991, pp. 794-798.

Tiligada, Chemotherapy: Induction of Stress Responses in: Endocrine-Related Cancer, Endocrine-Related Cancer, vol. 13, No. Supplement_1, Dec. 2006, pp. S115-S124.

Toyokuni, Persistent Oxidative Stress in Cancer, FEBS Letters, vol. 358, No. 1, Jan. 16, 1995, pp. 1-3.

Trachootham et al., Targeting Cancer Cells by ROS-Mediated Mechanisms: a Radical Therapeutic Approach?, Nature Reviews, vol. 8, No. 7, Jul. 2009, pp. 579-591.

Trott et al., Autodock Vina: Improving the Speed and Accuracy of Docking with a New Scoring Function, Efficient Optimization and Multithreading, J. Comput. Chem., vol. 31, No. 2, Jan. 30, 2010, pp. 455-461.

Turrens et al., Generation of Superoxide Anion by the NADH Dehydrogenase of Bovine Heart Mitochondria, The Biochemical Society, vol. 191, No. 2, Nov. 1, 1980, pp. 421-427.

Xia et al., Crystal Structure of the Cytochrome bc1 Complex from Bovine Heart Mitochondria, Science, vol. 277, No. 5322, Jul. 4, 1997, pp. 60-66.

Zhang et al., Electron Transfer by Domain Movement in Cytochrome bc1, Nature, vol. 392, No. 6677, Apr. 16, 1998, pp. 677-684.

Zoete et al., SwissParam: A Fast Force Field Generation Tool for Small Organic Molecules, Journal of Computational Chemistry, vol. 32, No. 11, Aug. 2011, pp. 2360-2368.

* cited by examiner

FIG. 14
Class I
ZINC00045127
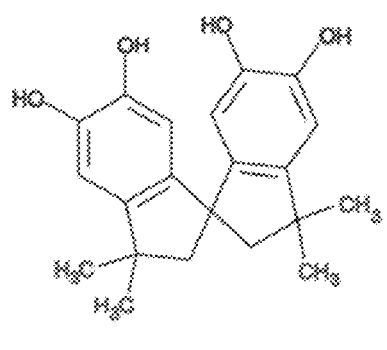
Class II
ZINC00627552
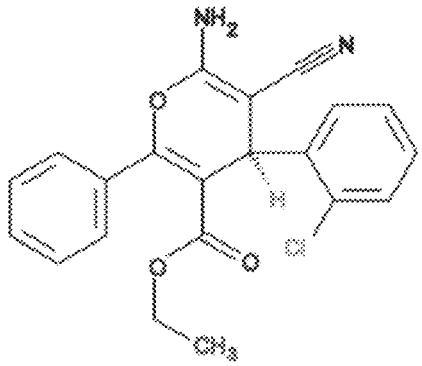
Class III
ZINC01611570
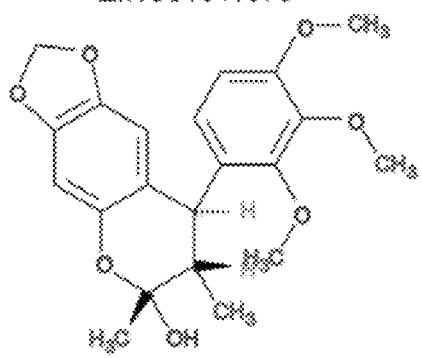
Class IV
ZINC03843643
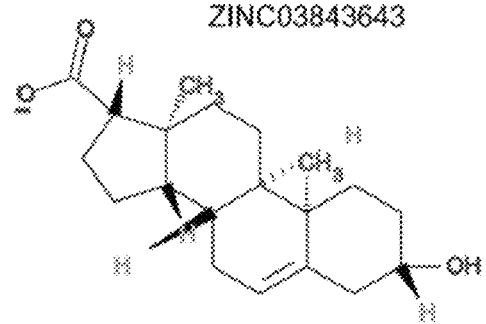

INHIBITION OF RESPIRATORY COMPLEX III BY LIGANDS THAT INTERACT WITH A REGULATORY SWITCH

CROSS-REFERENCE TO RELATED APPLICATIONS

The present application is a division of U.S. application Ser. No. 16/531,511, filed Aug. 5, 2019, which is a continuation of International Patent Application No. PCT/US2018/017638, filed Feb. 9, 2018, which claims priority to U.S. Provisional Appln. No. 62/457,684, filed Feb. 10, 2017, the disclosures of which are herein incorporated by reference in their entirety for all purposes.

STATEMENT AS TO RIGHTS TO INVENTIONS MADE UNDER FEDERALLY SPONSORED RESEARCH AND DEVELOPMENT

This invention was made with Government support under Grant No. GM054052 awarded by the National Institutes of Health (NIH). The Government has certain rights in the invention.

BACKGROUND OF THE INVENTION

Ideally, a smart anti-cancer drug should discriminate between cancer and normal cells. One of the recently discovered biochemical variations in cancer cells that distinguish them from normal cells is a higher basal level of reactive oxygen species (ROS), which makes the cancer cells more susceptible to ROS-induced apoptosis (Szatrowski and Nathan (1991) *Cancer Res.* 51:794; Kawanishi et al. (2006) *Biol. Chem.* 387:365; Toyokuni et al. (1995) *FEBS Lett.* 358:1; and Trachootham et al. (2009) *Nat. Rev. Drug Discov.* 8:579). However, since cancer cells can adapt to such oxidative stress by up-regulating antioxidant production (Tiligada (2006) *Endocrine Related Cancer* 13:S115), to make use of such a mechanism, a drug should induce rapid production and accumulation of ROS and trigger apoptosis in cancer cells before anti-oxidant up-regulation takes effect.

The mitochondrial electron transport chain (METC) is one of the major sources of ROS in the cell (Adam-Vizi and Chinopoulos (2006) *Trends Pharmacol. Sci.* 27:639; and Lenaz (2001) *IUBMB Life* 52:159), and respiratory complex III (also known as ubiquinol:cytochrome c oxidoreductase complex or $bc_1$ complex) is one of the two chief producers of ROS in METC (Turrens and Boveris (1980) *Biochem.* 1191:421; and Sugioka et al. (1988) *Biochim. Biophys. Acta* 936:377). Therefore, $bc_1$ complex is a natural target for any candidate anti-cancer drug whose function would be to increase ROS production and to bring it to an over-threshold level and thereby trigger apoptosis in cancer cells, while leaving the normal cells in under-threshold level of ROS (Trachootham et al. (2009) *Nat. Rev. Drug Discov.* 8:579). Moreover, $bc_1$ complex has a docking site for the water-soluble electron carrier cyctochrome c which plays a critical role in cell apoptosis (Jiang and Wang (2004) *Annu. Rev. Biochem.* 73:87). Thus, $bc_1$ complex has a dual role in this context: as a major site for ROS production which exerts a cytotoxic effect (Fruehauf and Myskens, Jr. (2007) *Clin. Cancer Res.* 13:789), and as a source of oxidative stress leading to cytochrome c-mediated cell apoptosis.

Located in the inner-mitochondrial membrane, $bc_1$ complex is the middle player in the electron transport proton pumping orchestra, which converts the free energy of redox reactions to an electrochemical proton gradient (Mitchell (1961) *Nature* 191:141 and Mitchell (1966) *Biol. Rev. Camb. Philos. Soc.* 41:445). The mitochondrial $bc_1$ complex has an intertwined dimeric structure comprised of 11 sub-units in each monomer, but only three of them have catalytic function. The core subunits include: the Rieske domain, which incorporates an iron-sulfur cluster [2Fe-2S]; the trans-membrane cytochrome b domain, incorporating a low-potential heme group (heme $b_L$) and a high-potential heme group (heme $b_H$); and the cytochrome ci domain, containing heme ci group and two separate binding sites, $Q_o$ (or $Q_P$) site where the hydrophobic electron carrier ubihydroquinol $QH_2$ is oxidized, and $Q_i$ (or $Q_N$) site where ubiquinone molecule Q is reduced (Xia et al. (1997) *Science* 277:60; Schagger et al. (1986) *Methods Enzymol.* 126:224; Zhang et al. (1998) *Nature* 392:677; and Iwata et al. (1998) *Science* 281:64).

Because of the relevance of respiratory complex III to ROS-induced apoptosis of cancer cells, study of the enzyme has been an active field of research. U.S. Patent Application Publication No. 2005/0019766 describes the characterization of mutants in the genes isp-1 and ctb-1, which are genes that have a function at the level of cellular physiology, mitochondrial respiration and electron transport, and resistance to oxidative stress, as well as regulating developmental, behavioral, reproductive and aging rates. U.S. Patent Application Publication No. 2008/0280294 describes a method for identifying a subject likely to have, or at risk of developing a disease condition correlated with increased ROS, including cancer, by identifying in the subject a missense mutation in a nucleic acid of complex III, IV and/or V of the oxidative phosphorylation system. U.S. Patent Application Publication No. 2011/0144192 describes a method for modulating or controlling sodium channel current of a cell including inducing mitochondrial ROS production in the cell. U.S. Pat. No. 8,815,844 describes inhibitors of the activity of the electron transport chains and/or the mitochondrial TCA cycle in glioma-initiating cells (GICs) for use in a method for preventing and/or treating tumors presenting glioma-initiating cells (GICs) in a subject who has undergone a prior removal of a tumor glioma bulk.

Even in view of these references, the need exists for novel inhibitors of the activity of the mitochondrial electron transport chain. Accordingly, in addition to fulfilling other needs, the present invention provides methods for inhibiting respiratory complex III. As such, the present invention provides methods that can be useful as therapies for disorders such as cancer in patients.

BRIEF SUMMARY OF THE INVENTION

The present invention provides methods for using several ligand compounds to bind to respiratory complex III and inhibit the functioning of the complex. A newly identified binding site is located at the opposite side of the respiratory complex III enzyme with respect to the ubiquinol-binding site ($Q_o$ site), and distinctly different from both $Q_o$ and $Q_i$ sites (hence designated as Non-Q binding site, NQ). NQ-site binding pocket extends up close to Phe90 residue, an internal switch (LH switch) that regulates electron transfer between heme $b_L$ and heme $b_H$ of the low potential redox chain. Docking studies and molecular dynamics simulations of different molecules to NQ-site revealed potential ligands which exhibit a novel inhibitory effect for $bc_1$ complex by switching the LH switch to an "off" conformation, thereby significantly reducing electron transfer rate in the low potential redox chain. Moreover, the novel inhibitors have lower binding affinity for both $Q_o$ and $Q_i$ sites, and hence do not interfere with binding of the natural ligands to those sites. The inhibitory activity of those novel ligands in $bc_1$ complex can promote the production of reactive oxygen species (ROS) at the $Q_o$ site. Hence those ligands are potential candidates for designing new "mitocan" drugs.

In one aspect, the present invention provides a method of inhibiting respiratory complex III in a cell. The method includes contacting the cell with a compound such that the compound binds to respiratory complex III, thereby inhibiting respiratory complex III. The compound can have the structure:

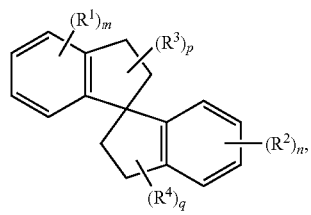

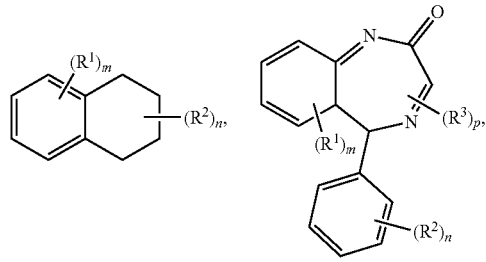

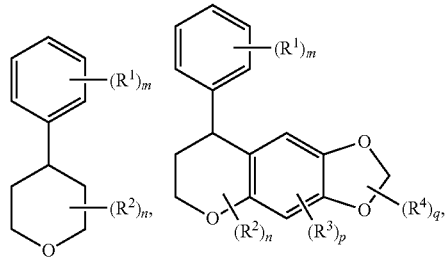

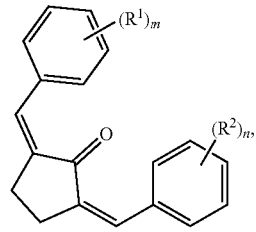

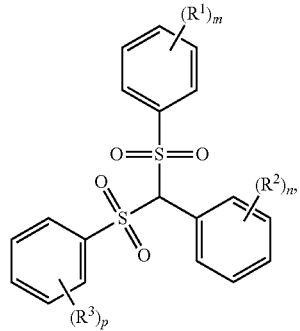

-continued

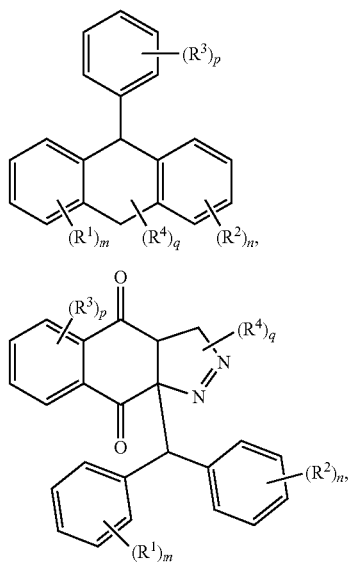

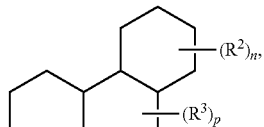

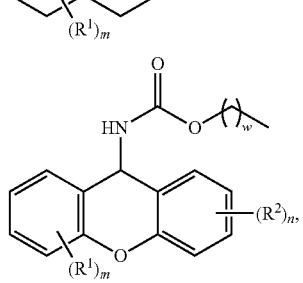

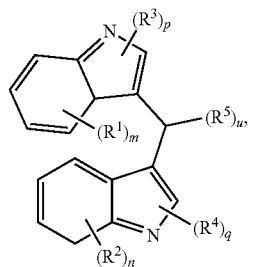

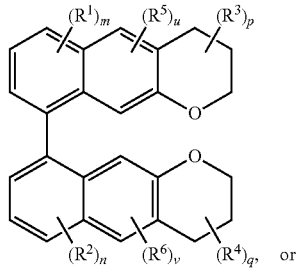

or

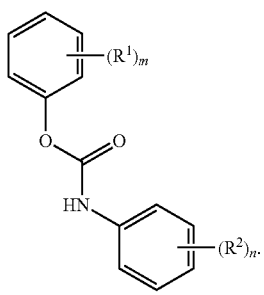

Each $R^1$, $R^2$, $R^3$, $R^4$, $R^5$, and $R^6$ can independently be hydrogen, $C_{1-6}$ alkyl, $C_{1-6}$ alkylhydroxy, $C_{1-6}$ haloalkyl, $C_{1-6}$ alkoxy, $C_{1-6}$ haloalkoxy, $C_{6-12}$ aryl, halogen, hydroxyl, oxide, —CN, —NH$_2$, —NO$_2$, and —C(O)—C$_{1-6}$ alkyl, or —C(O)O$^-$. The subscripts m and n can each independently be integers from 0 to 5. The subscript p is an integer from 0 to 4. The subscripts q, u, and v can each independently be integers from 0 to 2. The subscript w is an integer from 0 to 3.

In some embodiments, the compound enhances the production of reactive oxygen species (ROS) in the cell. In some embodiments, the cell is a cancer cell. In some embodiments, the cell is in a subject. In some embodiments, the method further includes administering an effective amount of the compound to the subject.

In a further aspect, the present invention provides a method of treating cancer in a subject. The method includes administering to the subject in need thereof, a therapeutically effective amount of a compound that can have the structure:

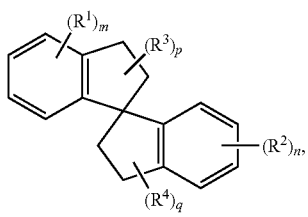

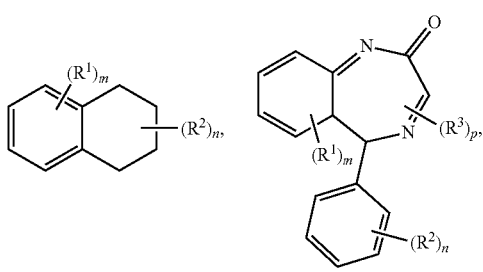

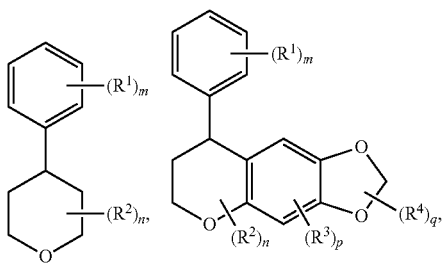

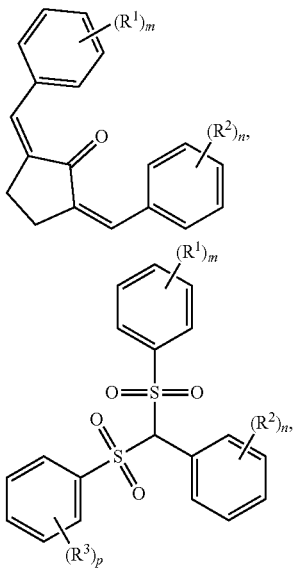

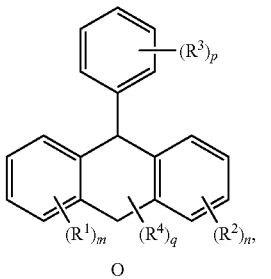

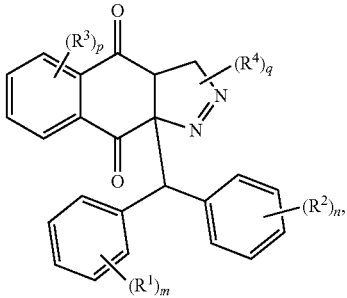

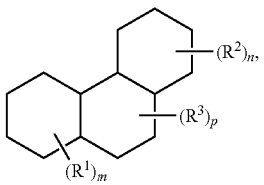

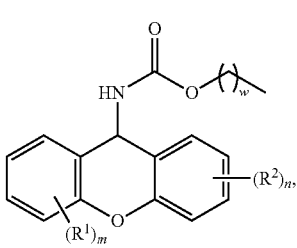

-continued

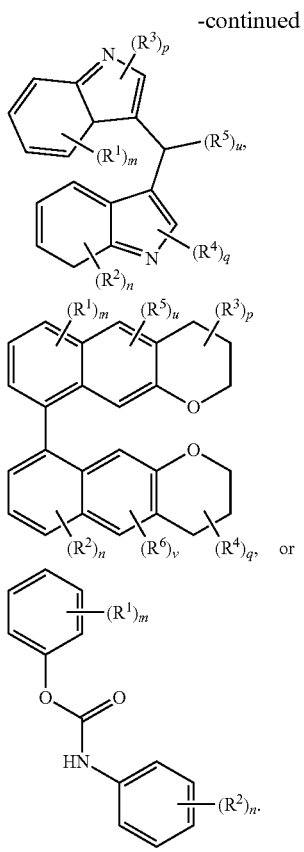

Each $R^1$, $R^2$, $R^3$, $R^4$, $R^5$, and $R^6$ can independently be hydrogen, $C_{1-6}$ alkyl, $C_{1-6}$ alkylhydroxy, $C_{1-6}$ haloalkyl, $C_{1-6}$ alkoxy, $C_{1-6}$ haloalkoxy, $C_{6-12}$ aryl, halogen, hydroxyl, oxide, —CN, —$NH_2$, —$NO_2$, and —C(O)—$C_{1-6}$ alkyl, and —C(O)O$^-$. The subscripts m and n can each independently be integers from 0 to 5. The subscript p is an integer from 0 to 4. The subscripts q, u, and v can each independently be integers from 0 to 2. The subscript w is an integer from 0 to 3.

Other objects, features, and advantages of the present invention will be apparent to one of skill in the art from the following detailed description and figures.

BRIEF DESCRIPTION OF THE DRAWINGS

FIG. 9A: plots of the total distance between the corresponding ligand centroid and both heme b iron atoms along the 50 ns MD trajectory. FIG. 9B: plots of the corresponding ligand RMSD along the 50 ns MD trajectory. FIG. 9C: plots of the total distance between Phe90 centroid and both heme b porphyrin ring edges along the 50 ns MD trajectory. The baseline (=13.3 Å) equals to the distance found in Q-bound $bc_1$ structure (PDB: 1NTZ) (indicated by hashed line if total distance is lower than 13.3 Å).

FIG. 14 shows chemical structures of representative ligands in four classes.

DETAILED DESCRIPTION OF THE INVENTION

I. Introduction

Residue Phe90 plays the role of an intra-monomeric switch (designated as LH switch) which can regulate the rate of electron transfer between heme $b_L$ and heme $b_H$ of the $bc_1$ respiratory complex III (Hagras et al. (2016) *Biochim.*

Biophys. Acta 1857:749). Phe90 can exist in two conformations, designated as $OFF_{LH}$ and $ON_{LH}$. The binding of an aromatic ligand at $Q_o$ site switches the conformation of Phe90 from a tilted conformation ($OFF_{LH}$) to a parallel conformation ($ON_{LH}$), facilitating electron transfer reaction between heme $b_L$ and heme $b_H$. Being in the $OFF_{LH}$ conformation, the electron transfer rate diminishes by about three orders of magnitude compared to the Phe90 $ON_{LH}$ conformation. Modification of the conformation of the electron transfer switch can interfere with the trans-membrane ET reaction between heme $b_L$ and heme $b_H$ to slow it down, or shut it off completely. Such interference can lead to a greater localization of the second electron (transferred from $QH_2$ at $Q_o$ site) on heme $b_L$ and hence to a higher chance to be picked up by oxygen molecules leading to ROS production.

Figure 1:
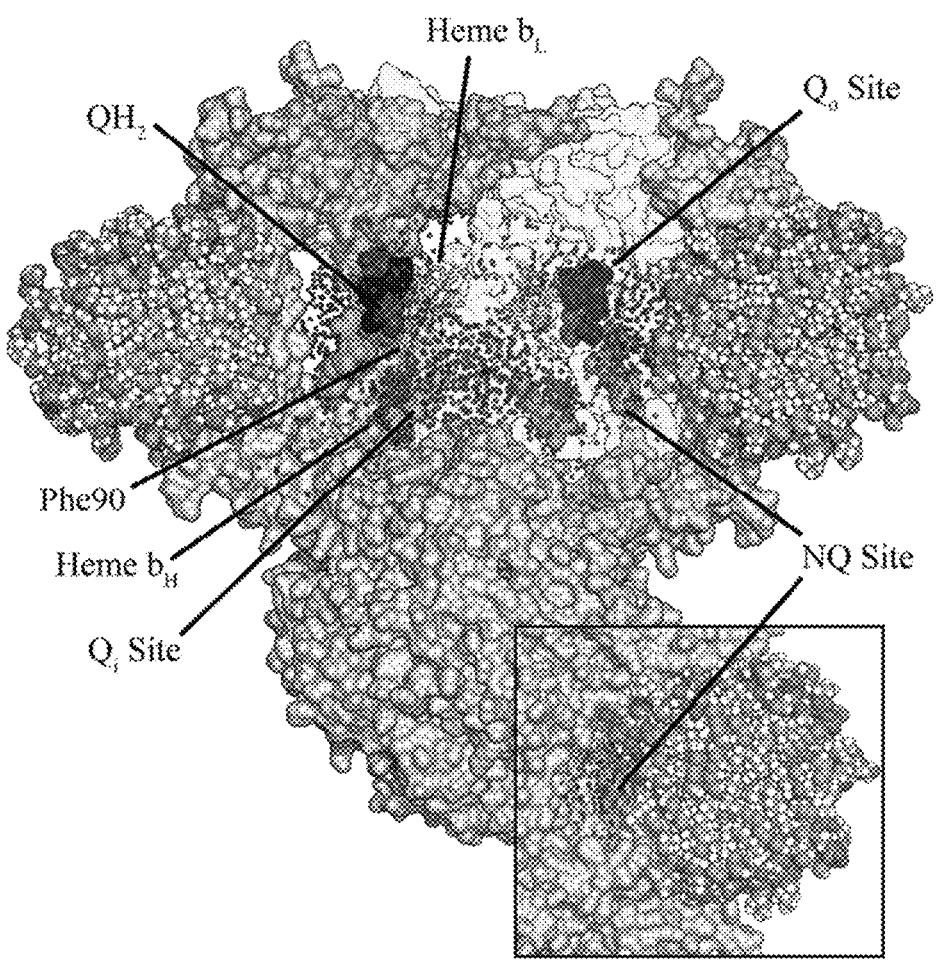
FIG. 1 illustrates the structure of the homodimer respiratory complex III embedded in the membrane where the chains of cytochrome b domain are either removed or transparent for clarity. Relative positions are shown of heme $b_L$ and heme $b_H$ with the intervening internal switch Phe90 residue. Different binding sites are visualized including $Q_o$ binding pocket as computed with AutoLigand occupied by $QH_2$ molecule (van der Waals spheres), Q molecule occupying $Q_i$ site (van der Waals spheres) and NQ site as computed by AutoLigand (van der Waals spheres). the inset, zoomed-in visualization of NQ site entrance is displayed.

A unique binding pocket extends deep into the enzyme body reaching the region of Phe90 switch. This new binding pocket (designated as NonQ-site or NQ-site for short) in the respiratory complex III complex is shown in FIG. 1. The NQ site is located at the opposite side of the enzyme with respect to $Q_o$ site; like $Q_o$, it is buried inside the inner-mitochondrial membrane, and its entrance is fully hydrated. In contrast to $Q_o$ site, however, the NQ-site penetrates deeply in the cytochrome b domain and reaches very closely the LH region. Hence the NQ-site provides a suitable binding pocket for ligands that can influence the orientation of Phe90 residue, and hence modulate the corresponding ET rate between heme $b_L$ and heme $b_H$.

A series of docking calculations and molecular dynamics simulations at the new docking site has led to a set of ligands that fix the Phe90 switch to its OFF position and hence significantly diminish the electron transfer rate between heme $b_L$ and heme $b_H$. The inhibiting ligands can result in a major increase of ROS production by the enzyme, and thus can be utilized to design a smart mitocan drug.

II. Definitions

As used herein, the following terms have the meanings ascribed to them unless specified otherwise.

The term "administering" refers to oral administration, administration as a suppository, topical contact, parenteral, intravenous, intraperitoneal, intramuscular, intralesional, intranasal or subcutaneous administration, intrathecal administration, or the implantation of a slow-release device e.g., a mini-osmotic pump, to the subject.

The term "subject" refers to animals such as mammals, including, but not limited to, primates (e.g., humans), cows, sheep, goats, horses, dogs, cats, rabbits, rats, mice and the like. In certain embodiments, the subject is a human.

The terms "therapeutically effective amount or dose" or "therapeutically sufficient amount or dose" or "effective or sufficient amount or dose" refer to a dose that produces therapeutic effects for which it is administered. The exact dose will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy*, 20th Edition, 2003, Gennaro, Ed., Lippincott, Williams & Wilkins). In sensitized cells, the therapeutically effective dose can often be lower than the conventional therapeutically effective dose for non-sensitized cells.

The term "alkyl" refers to a straight or branched, saturated, aliphatic radical having the number of carbon atoms indicated. Alkyl can include any number of carbons, such as $C_{1-2}$, $C_{1-3}$, $C_{1-4}$, $C_{1-5}$, $C_{1-6}$, $C_{1-7}$, $C_{1-8}$, $C_{1-9}$, $C_{1-10}$, $C_{2-3}$, $C_{2-4}$, $C_{2-5}$, $C_{2-6}$, $C_{3-4}$, $C_{3-5}$, $C_{3-6}$, $C_{4-5}$, $C_{4-6}$ and $C_{5-6}$. For example, $C_{1-6}$ alkyl includes, but is not limited to, methyl, ethyl, propyl, isopropyl, butyl, isobutyl, sec-butyl, tert-butyl, pentyl, isopentyl, hexyl, etc. Alkyl can also refer to alkyl groups having up to 20 carbons atoms, such as, but not limited to heptyl, octyl, nonyl, decyl, etc. Alkyl groups can be substituted or unsubstituted.

The term "alkylhydroxy" refers to an alkyl group, as defined above, where at least one of the hydrogen atoms is replaced with a hydroxy group. As for the alkyl group, alkylhydroxy groups can have any suitable number of carbon atoms, such as $C_{1-6}$. Exemplary alkylhydroxy groups include, but are not limited to, hydroxy-methyl, hydroxy-ethyl (where the hydroxy is in the 1- or 2-position), hydroxy-propyl (where the hydroxy is in the 1-, 2- or 3-position), hydroxybutyl (where the hydroxy is in the 1-, 2-, 3- or 4-position), hydroxypentyl (where the hydroxy is in the 1-, 2-, 3-, 4- or 5-position), hydroxyhexyl (where the hydroxy is in the 1-, 2-, 3-, 4-, 5- or 6-position), 1,2-dihydroxyethyl, and the like.

The term "alkoxy" refers to an alkyl group having an oxygen atom that connects the alkyl group to the point of attachment: alkyl-O—. As for alkyl group, alkoxy groups can have any suitable number of carbon atoms, such as $C_{1-6}$. Alkoxy groups include, for example, methoxy, ethoxy, propoxy, iso-propoxy, butoxy, 2-butoxy, iso-butoxy, sec-butoxy, tert-butoxy, pentoxy, hexoxy, etc. The alkoxy groups can be further substituted with a variety of substituents described within. Alkoxy groups can be substituted or unsubstituted.

The term "haloalkyl" refers to alkyl, as defined above, where some or all of the hydrogen atoms are replaced with halogen atoms. As for alkyl group, haloalkyl groups can have any suitable number of carbon atoms, such as $C_{1-6}$. For example, haloalkyl includes trifluoromethyl, flouromethyl, etc. In some instances, the term "perfluoro" can be used to define a compound or radical where all the hydrogens are replaced with fluorine. For example, perfluoromethyl refers to 1,1,1-trifluoromethyl.

The term "haloalkoxy" refers to an alkoxy group where some or all of the hydrogen atoms are substituted with halogen atoms. As for an alkyl group, haloalkoxy groups can have any suitable number of carbon atoms, such as $C_{1-6}$. The alkoxy groups can be substituted with 1, 2, 3, or more halogens. When all the hydrogens are replaced with a halogen, for example by fluorine, the compounds are per-substituted, for example, perfluorinated. Haloalkoxy includes, but is not limited to, trifluoromethoxy, 2,2,2,-trifluoroethoxy, perfluoroethoxy, etc.

The term "aryl" refers to an aromatic ring system having any suitable number of ring atoms and any suitable number of rings. Aryl groups can include any suitable number of ring atoms, such as, 6, 7, 8, 9, 10, 11, 12, 13, 14, 15 or 16 ring atoms, as well as from 6 to 10, 6 to 12, or 6 to 14 ring members. Aryl groups can be monocyclic, fused to form bicyclic or tricyclic groups, or linked by a bond to form a biaryl group. Representative aryl groups include phenyl, naphthyl and biphenyl. Other aryl groups include benzyl, having a methylene linking group. Some aryl groups have from 6 to 12 ring members, such as phenyl, naphthyl or biphenyl. Other aryl groups have from 6 to 10 ring members, such as phenyl or naphthyl. Some other aryl groups have 6 ring members, such as phenyl. Aryl groups can be substituted or unsubstituted.

The term "halogen" refers to fluorine, chlorine, bromine and iodine.

The term "cancer" is intended to include any member of a class of diseases characterized by the uncontrolled growth of aberrant cells. The term includes all known cancers and neoplastic conditions, whether characterized as malignant, benign, soft tissue, or solid, and cancers of all stages and grades including pre- and post-metastatic cancers. Examples of different types of cancer include, but are not limited to, breast cancer; lung cancer (e.g., non-small cell lung cancer); digestive and gastrointestinal cancers such as colorectal cancer, gastrointestinal stromal tumors, gastrointestinal carcinoid tumors, colon cancer, rectal cancer, anal cancer, bile duct cancer, small intestine cancer, and stomach (gastric) cancer; esophageal cancer; gallbladder cancer; liver cancer; pancreatic cancer; appendix cancer; ovarian cancer; renal cancer (e.g., renal cell carcinoma); cancer of the central nervous system; skin cancer; lymphomas; choriocarcinomas; head and neck cancers; osteogenic sarcomas; and blood cancers. As used herein, a "tumor" comprises one or more cancerous cells.

"Salt" refers to acid or base salts of the compounds used in the methods of the present invention. Illustrative examples of pharmaceutically acceptable salts are mineral acid (hydrochloric acid, hydrobromic acid, phosphoric acid, and the like) salts, organic acid (acetic acid, propionic acid, glutamic acid, citric acid and the like) salts, quaternary ammonium (methyl iodide, ethyl iodide, and the like) salts. It is understood that the pharmaceutically acceptable salts are non-toxic. Additional information on suitable pharmaceutically acceptable salts can be found in *Remington's Pharmaceutical Sciences,* 17th ed., Mack Publishing Company, Easton, Pa., 1985, which is incorporated herein by reference.

Pharmaceutically acceptable salts of the acidic compounds of the present invention are salts formed with bases, namely cationic salts such as alkali and alkaline earth metal salts, such as sodium, lithium, potassium, calcium, magnesium, as well as ammonium salts, such as ammonium, trimethyl-ammonium, diethylammonium, and tris-(hydroxymethyl)-methyl-ammonium salts.

Similarly acid addition salts, such as of mineral acids, organic carboxylic and organic sulfonic acids, e.g., hydrochloric acid, methanesulfonic acid, malefic acid, are also possible provided a basic group, such as pyridyl, constitutes part of the structure.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

The term "hydrate" refers to a compound that is complexed to at least one water molecule. The compounds of the present invention can be complexed with from 1 to 10 water molecules.

The term "isomers" refers to compounds with the same chemical formula but which are structurally distinguishable. Certain compounds of the present invention possess asymmetric carbon atoms (optical centers) or double bonds; the racemates, diastereomers, geometric isomers and individual isomers are all intended to be encompassed within the scope of the present invention.

The term "tautomer" refers to one of two or more structural isomers which exist in equilibrium and which are readily converted from one form to another. The present invention includes all tautomers and stereoisomers of compounds of the present invention, either in admixture or in pure or substantially pure form. The compounds of the present invention can have asymmetric centers at the carbon atoms, and therefore the compounds of the present invention can exist in diastereomeric or enantiomeric forms or mixtures thereof. All conformational isomers (e.g., cis and trans isomers) and all optical isomers (e.g., enantiomers and diastereomers), racemic, diastereomeric and other mixtures of such isomers, as well as solvates, hydrates, isomorphs, polymorphs and tautomers are within the scope of the present invention. Compounds according to the present invention can be prepared using diastereomers, enantiomers or racemic mixtures as starting materials. Furthermore, diastereomer and enantiomer products can be separated by chromatography, fractional crystallization or other methods known to those of skill in the art.

The terms "pharmaceutically acceptable excipient" and "pharmaceutically acceptable carrier" refer to a substance that aids the administration of an active agent to and absorption by a subject and can be included in the compositions of the present invention without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors and colors, and the like. One of skill in the art will recognize that other pharmaceutical excipients are useful in the present invention.

The term "contacting" refers to the process of bringing into contact at least two distinct species such that they can react with one another or interact such that one has an effect on the other. It should be appreciated, however, the resulting reaction product can be produced directly from a reaction between the added reagents or from an intermediate from one or more of the added reagents which can be produced in the reaction mixture.

The terms "treat", "treating" and "treatment" refer to any indicia of success in the treatment or amelioration of an injury, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or a psychiatric evaluation.

The terms "patient" or "subject in need thereof" refers to a living organism suffering from or prone to a condition that can be treated by administration of a pharmaceutical composition as provided herein. Non-limiting examples include humans, other mammals and other non-mammalian animals.

The terms "disorder" or "condition" refer to a state of being or health status of a patient or subject capable of being treated with the galectin-1 (gal-1) inhibitors of the present invention. Examples of disorders or conditions include, but are not limited to, ovarian cancer, prostate cancer, lung cancer, breast cancer, kidney cancer, pancreatic cancer, colon cancer, and non-small cell lung cancer.

The term "chemotherapeutic agent" refers to a compound or pharmaceutical composition useful for treating or ameliorating cancer. The agent can be given with a curative intent, with an aim to prolong life, or for the purpose of reducing symptoms.

III. Methods for Inhibition

In one aspect, the present invention provides several methods for inhibiting respiratory complex III in a cell. The methods include contacting a cell with a compound that can having the structure:

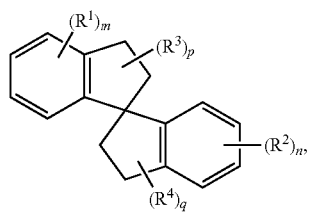

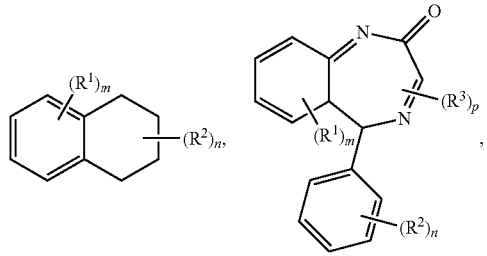

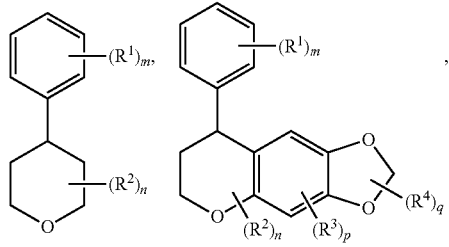

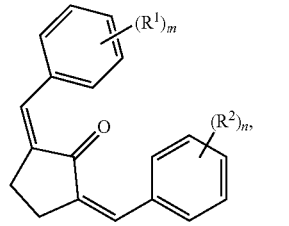

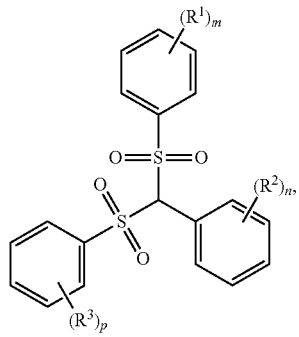

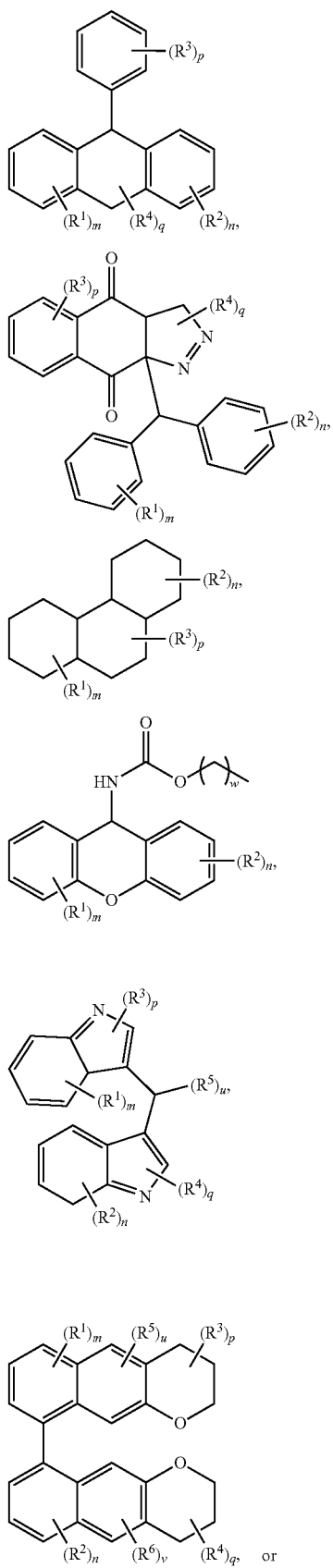

-continued

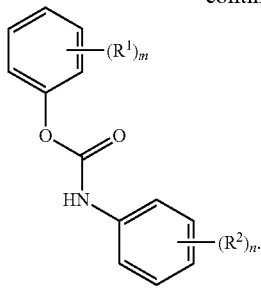

Each $R^1$, $R^2$, $R^3$, $R^4$, $R^5$, and $R^6$ can independently be hydrogen, $C_{1-6}$ alkyl, $C_{1-6}$ alkylhydroxy, $C_{1-6}$ haloalkyl, $C_{1-6}$ alkoxy, $C_{1-6}$ haloalkoxy, $C_{6-12}$ aryl, halogen, hydroxyl, oxide, —CN, —NH$_2$, —NO$_2$, and —C(O)—C$_{1-6}$ alkyl, or —C(O)O$^-$. The subscripts m and n can each independently be integers from 0 to 5. The subscript p is an integer from 0 to 4. The subscripts q, u, and v can each independently be integers from 0 to 2. The subscript w is an integer from 0 to 3.

In some embodiments, each $R^1$ of the compound is independently hydrogen, $C_{1-6}$ alkyl, $C_{1-6}$ alkylhydroxy, $C_{1-6}$ haloalkyl, $C_{1-6}$ alkoxy, $C_{1-6}$ haloalkoxy, $C_{6-12}$ aryl, halogen, hydroxyl, oxide, —CN, —NH$_2$, —NO$_2$, and —C(O)—C$_{1-6}$ alkyl, or —C(O)O$^-$. In some embodiments, each $R^1$ is independently hydrogen, $C_{1-6}$ alkyl, $C_{1-6}$ alkoxy, halogen, hydroxyl, —NO$_2$, or —C(O)—C$_{1-6}$ alkyl. In some embodiments, each $R^1$ is independently $C_{1-6}$ alkyl, halogen, hydroxyl, or —C(O)—C$_{1-6}$ alkyl. In some embodiments, each $R^1$ is independently $C_{1-6}$ alkyl, $C_{1-6}$ alkylhydroxy, or hydroxyl. In some embodiments, each $R^1$ is independently —NO$_2$ or $C_{1-6}$ alkoxy. In some embodiments, each $R^1$ is independently $C_{1-6}$ alkoxy or hydroxyl. In some embodiments, each $R^1$ is independently $C_{1-6}$ alkoxy. In some embodiments, each $R^1$ is independently halogen. In some embodiments, $R^1$ is butyl. In some embodiments, $R^1$ of formula is chlorine. In some embodiments, $R^1$ of formula is hydroxyl. In some embodiments, $R^1$ is methoxy. In some embodiments, $R^1$ is —NO$_2$. In some embodiments, $R^1$ is methylhydroxy.

In some embodiments, each $R^2$ of the compound is independently hydrogen, $C_{1-6}$ alkyl, $C_{1-6}$ alkylhydroxy, $C_{1-6}$ haloalkyl, $C_{1-6}$ alkoxy, $C_{1-6}$ haloalkoxy, $C_{6-12}$ aryl, halogen, hydroxyl, oxide, —CN, —NH$_2$, —NO$_2$, and —C(O)—C$_{1-6}$ alkyl, or —C(O)O$^-$. In some embodiments, each $R^2$ is independently hydrogen, $C_{1-6}$ alkyl, $C_{1-6}$ alkoxy, $C_{6-12}$ aryl, hydroxyl, —CN, —NH$_2$, —C(O)O—C$_{1-6}$ alkyl, or —C(O)O$^-$. In some embodiments, each $R^2$ of is independently $C_{6-12}$ aryl, —CN, —NH$_2$, or —C(O)O—C$_{1-6}$ alkyl. In some embodiments, each $R^2$ is independently —NO$_2$ or $C_{1-6}$ alkoxy. In some embodiments, each $R^2$ is independently $C_{1-6}$ alkyl or hydroxyl. In some embodiments, each $R^2$ is independently hydroxyl or C(O)O$^-$. In some embodiments, each $R^2$ is independently $C_{1-6}$ alkyl. In some embodiments, $R^2$ is methyl. In some embodiments, $R^2$ is propyl. In some embodiments, $R^2$ is hydroxyl. In some embodiments, $R^2$ is phenyl. In some embodiments, $R^2$ is —CN. In some embodiments, $R^2$ is —NH$_2$. In some embodiments, $R^2$ is —C(O)O-ethyl. In some embodiments, $R^2$ is —NO$_2$. In some embodiments, $R^2$ is methoxy. In some embodiments, $R^2$ is C(O)O$^-$.

In some embodiments, each $R^3$ of the compound is independently hydrogen, $C_{1-6}$ alkyl, $C_{1-6}$ alkylhydroxy, $C_{1-6}$ haloalkyl, $C_{1-6}$ alkoxy, $C_{1-6}$ haloalkoxy, $C_{6-12}$ aryl, halogen, hydroxyl, oxide, —CN, —NH$_2$, —NO$_2$, and —C(O)—C$_{1-6}$ alkyl, or —C(O)O$^-$. In some embodiments, each $R^3$ is independently hydrogen, $C_{1-6}$ alkyl, $C_{1-6}$alkoxy, or oxide. In some embodiments, each $R^3$ is independently $C_{1-6}$ alkyl or oxide. In some embodiments, each $R^3$ is independently $C_{1-6}$ alkyl. In some embodiments, $R^3$ is $C_{1-6}$ alkoxy. In some embodiments, each $R^3$ is independently halogen. In some embodiments, $R^3$ is methyl. In some embodiments, $R^3$ is chlorine. In some embodiments, $R^3$ is oxide. In some embodiments, $R^3$ is methoxy.

In some embodiments, each $R^4$ of the compound is independently hydrogen, $C_{1-6}$ alkyl, $C_{1-6}$ alkylhydroxy, $C_{1-6}$ haloalkyl, $C_{1-6}$ alkoxy, $C_{1-6}$ haloalkoxy, $C_{6-12}$ aryl, halogen, hydroxyl, oxide, —CN, —NH$_2$, —NO$_2$, and —C(O)—C$_{1-6}$ alkyl, or —C(O)O$^-$. In some embodiments, each $R^4$ is independently hydrogen or $C_{1-6}$ alkyl. In some embodiments, each $R^4$ is independently $C_{1-6}$ alkyl. In some embodiments, each $R^4$ is methyl.

In some embodiments, each $R^5$ of the compound is independently hydrogen, $C_{1-6}$ alkyl, $C_{1-6}$ alkylhydroxy, $C_{1-6}$ haloalkyl, $C_{1-6}$ alkoxy, $C_{1-6}$ haloalkoxy, $C_{6-12}$ aryl, halogen, hydroxyl, oxide, —CN, —NH$_2$, —NO$_2$, and —C(O)—C$_{1-6}$ alkyl, or —C(O)O$^-$. In some embodiments, each $R^5$ is independently $C_{1-6}$ alkyl or —C(O)O$^-$. In some embodiments, $R^5$ is methyl. In some embodiments, $R^5$ is —C(O)O$^-$. In some embodiments, $R^5$ is hydroxyl.

In some embodiments, each $R^6$ of the compound is independently hydrogen, $C_{1-6}$ alkyl, $C_{1-6}$ alkylhydroxy, $C_{1-6}$ haloalkyl, $C_{1-6}$ alkoxy, $C_{1-6}$ haloalkoxy, $C_{6-12}$ aryl, halogen, hydroxyl, oxide, —CN, —NH$_2$, —NO$_2$, and —C(O)—C$_{1-6}$ alkyl, or —C(O)O$^-$. In some embodiments, $R^6$ is hydroxyl.

In some embodiments, subscripts m and n are each independently integers from 0 to 5. In some embodiments, subscript m is 0, 1, 2, 3, 4, or 5. In some embodiments, subscript m is 3. In some embodiments, subscript m is 2. In some embodiments, subscript m is 1. In some embodiments, subscript m is 0. The subscript n can be 0, 1, 2, 3, 4, or 5. In some embodiments, subscript n is 4. In some embodiments, subscript n is 3. In some embodiments, subscript n is 2. In some embodiments, subscript n is 1. In some embodiments, subscript n is 0. The subscript p can be an integer from 0 to 4. In some embodiments, subscript p is 0, 1, 2, 3, or 4. In some embodiments, subscript p is 2. In some embodiments, subscript p is 1. In some embodiments, subscript p is 0. In some embodiments, the subscripts q, u, and v are each independently integers from 0 to 2. In some embodiments, subscript q is 0, 1, or 2. In some embodiments, subscript q is 2. In some embodiments, subscript q is 0. In some embodiments, subscript u is 0, 1, or 2. In some embodiments, subscript u is 2. In some embodiments, subscript v is 0, 1, or 2. In some embodiments, subscript v is 1. In some embodiments, the subscript w is an integer from 0 to 3. In some embodiments, subscript w is 0, 1, 2, or 3. In some embodiments, subscript w is 1.

In some embodiments, the compound has the structure of formula I:

(I)

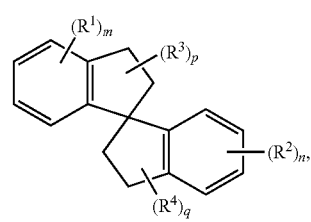

wherein each $R^1$ can independently be hydrogen, $C_{1-6}$ alkyl, $C_{1-6}$ alkoxy, halogen, hydroxyl, —$NO_2$, or —C(O)—$C_{1-6}$ alkyl. Each $R^2$ of formula I can independently be hydrogen, $C_{1-6}$ alkyl, $C_{1-6}$ alkoxy, $C_{6-12}$ aryl, hydroxyl, —CN, —$NH_2$, —C(O)O—$C_{1-6}$ alkyl, or —C(O)$O^-$. Each $R^3$ of formula I can independently be hydrogen, $C_{1-6}$ alkyl, $C_{1-6}$ alkoxy, or oxide. Each $R^4$ of formula I can independently be hydrogen or $C_{1-6}$ alkyl. The subscripts m and n of formula I can each independently be integers from 0 to 5. The subscript p of formula I can be an integer from 0 to 4. The subscript q of formula I can be an integer from 0 to 2.

In some embodiments, $R^1$ of formula I is hydroxyl. In some embodiments, $R^2$ of formula I is hydroxyl. In some embodiments, each $R^3$ of formula I is independently $C_{1-6}$ alkyl. In some embodiments, $R^3$ of formula I is methyl. In some embodiments, each $R^4$ of formula I is independently $C_{1-6}$ alkyl. In some embodiments, $R^4$ of formula I is methyl. In some embodiments, the subscript m of formula I is 2. In some embodiments, the subscript n of formula I is 2. In some embodiments, the subscript p of formula I is 2. In some embodiments, the subscript q of formula I is 2. In some embodiments, the compound of formula I is:

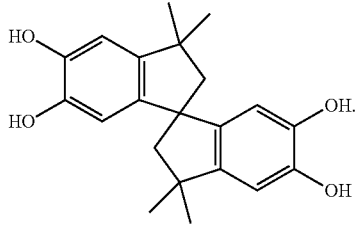

(ZINC0045127)

In some embodiments, the compound has the structure of formula II:

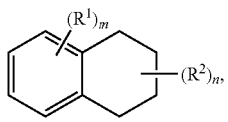

(II)

wherein each $R^1$ can independently be hydrogen, $C_{1-6}$ alkyl, $C_{1-6}$ alkoxy, halogen, hydroxyl, —$NO_2$, or —C(O)—$C_{1-6}$ alkyl. Each $R^2$ of formula II can independently be hydrogen, $C_{1-6}$ alkyl, $C_{1-6}$ alkoxy, $C_{6-12}$ aryl, hydroxyl, —CN, —$NH_2$, —C(O)O—$C_{1-6}$ alkyl, or —C(O)$O^-$. The subscripts m and n of formula II can each independently be integers from 0 to 5.

In some embodiments, each $R^1$ of formula II is independently $C_{1-6}$ alkyl, halogen, hydroxyl, or —C(O)—$C_{1-6}$ alkyl. In some embodiments, $R^1$ of formula II is butyl. In some embodiments, $R^1$ of formula II is ethyl. In some embodiments, $R^1$ of formula II is —C(O)— methyl. In some embodiments, $R^1$ of formula II is hydroxyl. In some embodiments, each $R^2$ of formula II is independently $C_{1-6}$ alkyl. In some embodiments, $R^2$ of formula II is methyl. In some embodiments, the subscripts m and n of formula II are each independently integers from 2 to 5. In some embodiments, subscript m of formula II is 2. In some embodiments, subscript n of formula II is 5. In some embodiments, subscript n is 4. In some embodiments, the compound of formula II is:

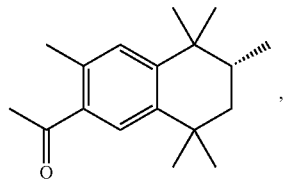

(ZINC01323080)

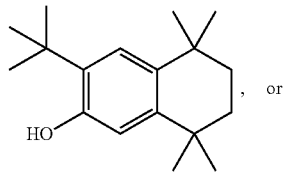

(ZINC01701287)

, or

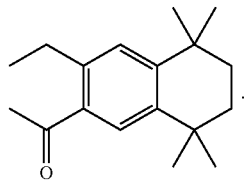

(ZINC01706901)

In some embodiments, the compound has the structure of formula III:

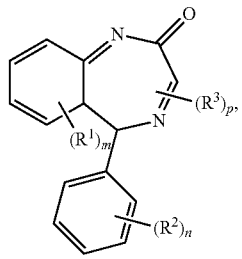

(III)

wherein each $R^1$ can independently be hydrogen, $C_{1-6}$ alkyl, $C_{1-6}$ alkoxy, halogen, hydroxyl, —$NO_2$, or —C(O)—$C_{1-6}$ alkyl. Each $R^2$ of formula III can independently be hydrogen, $C_{1-6}$ alkyl, $C_{1-6}$ alkoxy, $C_{6-12}$ aryl, hydroxyl, —CN, —$NH_2$, —C(O)O—$C_{1-6}$ alkyl, or —C(O)$O^-$. Each $R^3$ of formula III can independently be hydrogen, $C_{1-6}$ alkyl, $C_{1-6}$ alkoxy, or oxide. The subscripts m and n of formula III can each independently be integers from 0 to 5. The subscript p of formula III is an integer from 0 to 4.

In some embodiments, $R^1$ of formula III is halogen. In some embodiments, $R^1$ of formula III is chlorine. In some embodiments, each $R^3$ of formula III is independently $C_{1-6}$ alkyl or oxide. In some embodiments, $R^3$ of formula III is methyl. In some embodiments, $R^3$ of formula III is oxide. In some embodiments, subscript m of formula III is 1. In some embodiments, subscript n of formula III is 0. In some embodiments, subscript p of formula III is 2. In some embodiments, the compound of formula III is:

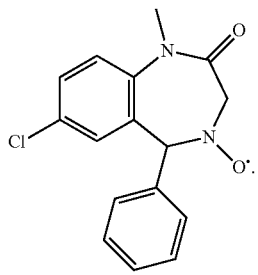

(ZINC01677767)

In some embodiments, the compound has the structure of formula IV:

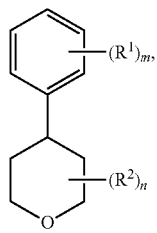

(IV)

wherein each $R^1$ is independently hydrogen, $C_{1-6}$ alkyl, $C_{1-6}$ alkoxy, halogen, hydroxyl, —$NO_2$, or —C(O)—$C_{1-6}$ alkyl. Each $R^2$ of formula IV is independently hydrogen, $C_{1-6}$ alkyl, $C_{1-6}$ alkoxy, $C_{6-12}$ aryl, hydroxyl, —CN, —$NH_2$, —C(O)O—$C_{1-6}$ alkyl, or —C(O)O$^-$. The subscripts m and n of formula IV are each independently integers from 0 to 5.

In some embodiments, $R^1$ of formula IV is halogen. In some embodiments, $R^1$ of formula IV is chlorine. In some embodiments, each $R^2$ of formula IV is independently $C_{6-12}$ aryl, —CN, —$NH_2$, or —C(O)O—$C_{1-6}$ alkyl. In some embodiments, $R^2$ of formula IV is phenyl. In some embodiments, $R^2$ of formula IV is —CN. In some embodiments, $R^2$ of formula IV is —$NH_2$. In some embodiments, $R^2$ of formula IV is —C(O)O-ethyl. In some embodiments, subscript m of formula IV is 1. In some embodiments, subscript n of formula IV is 4. In some embodiments, the compound of formula IV is:

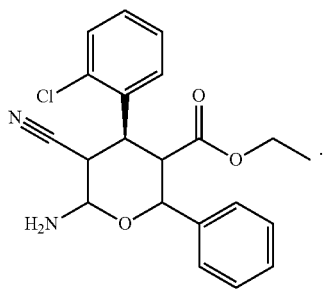

(ZINC00627552)

In some embodiments, the compound has the structure of formula V:

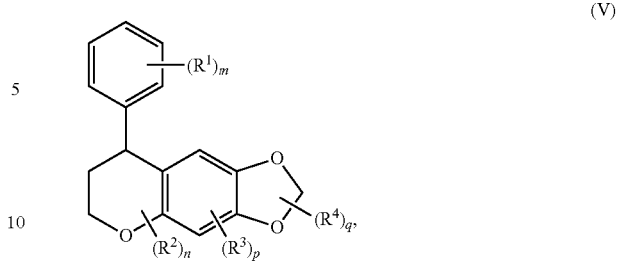

(V)

wherein each $R^1$ is independently hydrogen, $C_{1-6}$ alkyl, $C_{1-6}$ alkoxy, halogen, hydroxyl, —$NO_2$, or —C(O)—$C_{1-6}$ alkyl. Each $R^2$ of formula V is independently hydrogen, $C_{1-6}$ alkyl, $C_{1-6}$ alkoxy, $C_{6-12}$ aryl, hydroxyl, —CN, —$NH_2$, —C(O)O—$C_{1-6}$ alkyl, or —C(O)O$^-$. Each $R^3$ of formula V is independently hydrogen, $C_{1-6}$ alkyl, $C_{1-6}$ alkoxy, or oxide. Each $R^4$ of formula V is independently hydrogen or $C_{1-6}$ alkyl. Subscripts m and n of formula V are each independently integers from 0 to 5. Subscript p of formula V is an integer from 0 to 4. Subscript q of formula V is an integer from 0 to 2.

In some embodiments, each $R^1$ of formula V is independently $C_{1-6}$ alkoxy. In some embodiments, $R^1$ of formula V is methoxy. In some embodiments, each $R^2$ of formula V is independently $C_{1-6}$ alkyl or hydroxyl. In some embodiments, $R^2$ of formula V is methyl. In some embodiments, $R^2$ of formula V is hydroxyl. In some embodiments, subscript m of formula V is 3. In some embodiments, subscript n of formula V is 3. In some embodiments, subscript p of formula V is 0. In some embodiments, subscript q of formula V is 0. In some embodiments, the compound of formula V is:

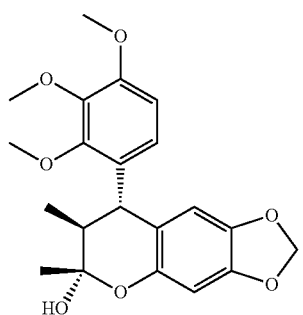

(ZINC01611570)

In some embodiments, the compound has the structure of formula VI:

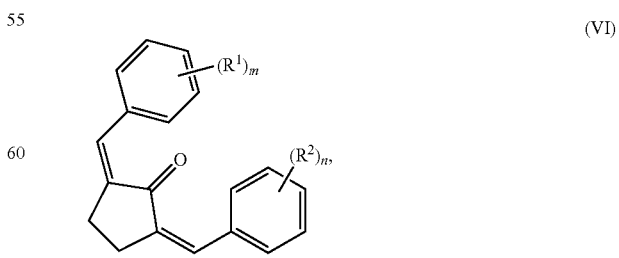

(VI)

wherein each $R^1$ is independently hydrogen, $C_{1-6}$ alkyl, $C_{1-6}$ alkoxy, halogen, hydroxyl, —$NO_2$, or —C(O)—$C_{1-6}$ alkyl.

Each $R^2$ of formula VI is independently hydrogen, $C_{1-6}$ alkyl, $C_{1-6}$ alkoxy, $C_{6-12}$ aryl, hydroxyl, —CN, —NH$_2$, —C(O)O—C$_{1-6}$ alkyl, or —C(O)O$^-$. The subscripts m and n of formula VI are each independently integers from 0 to 5.

In some embodiments, each $R^1$ of formula VI is independently —NO$_2$ or $C_{1-6}$ alkoxy. In some embodiments, $R^1$ of formula VI is —NO$_2$. In some embodiments, $R^1$ of formula VI is methoxy. In some embodiments, each $R^2$ of formula VI is independently —NO$_2$ or $C_{1-6}$ alkoxy. In some embodiments, $R^2$ of formula VI is —NO$_2$. In some embodiments, $R^2$ of formula VI is methoxy. In some embodiments, subscript m of formula VI is 1. In some embodiments, subscript n of formula VI is 1. In some embodiments, the compound of formula VI is:

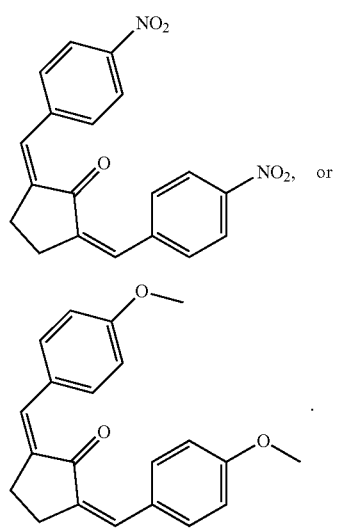

(ZINC01685490)

(ZINC16968711)

In some embodiments, the compound has the structure of formula VII:

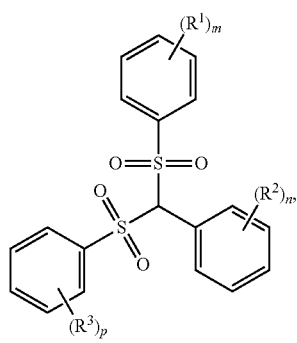

(VII)

wherein each $R^1$ is independently hydrogen, $C_{1-6}$ alkyl, $C_{1-6}$ alkoxy, halogen, hydroxyl, —NO$_2$, or —C(O)—$C_{1-6}$ alkyl. Each $R^2$ of formula VII is independently hydrogen, $C_{1-6}$ alkyl, $C_{1-6}$ alkoxy, $C_{6-12}$ aryl, hydroxyl, —CN, —NH$_2$, —C(O)O—$C_{1-6}$ alkyl, or —C(O)O$^-$. Each $R^3$ of formula VII is independently hydrogen, $C_{1-6}$ alkyl, $C_{1-6}$ alkoxy, or oxide. The subscripts m and n of formula VII are each independently integers from 0 to 5.

In some embodiments, $R^2$ of formula VII is C(O)O$^-$. In some embodiments, subscript m is 0. In some embodiments, subscript n of formula VII is 1. In some embodiments, subscript p of formula VII is 0. In some embodiments, the compound of formula VII is:

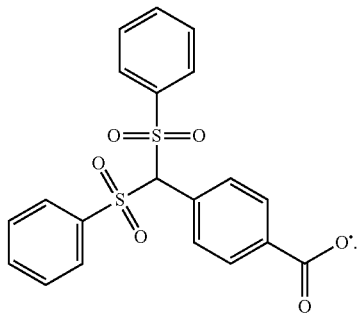

(ZINC01718184)

In some embodiments, the compound has the structure of formula VIII:

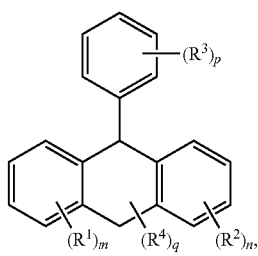

(VIII)

wherein each $R^1$ is independently hydrogen, $C_{1-6}$ alkyl, $C_{1-6}$ alkoxy, halogen, hydroxyl, —NO$_2$, or —C(O)—$C_{1-6}$ alkyl. Each $R^2$ of formula VIII is independently hydrogen, $C_{1-6}$ alkyl, $C_{1-6}$ alkoxy, $C_{6-12}$ aryl, hydroxyl, —CN, —NH$_2$, —C(O)O—$C_{1-6}$ alkyl, or —C(O)O$^-$. Each $R^3$ of formula VIII is independently hydrogen, $C_{1-6}$ alkyl, $C_{1-6}$ alkoxy, or oxide. Each $R^4$ of formula VIII is independently hydrogen or $C_{1-6}$ alkyl. The subscripts m and n of formula VIII are each independently integers from 0 to 5. The subscript p of formula VIII is an integer from 0 to 4. The subscript q of formula VIII is an integer from 0 to 2.

In some embodiments, each $R^1$ of formula VIII is independently $C_{1-6}$ alkoxy or hydroxyl. In some embodiments, $R^1$ of formula VIII is methoxy. In some embodiments, $R^1$ of formula VIII is hydroxyl. In some embodiments, each $R^2$ of formula VIII is independently $C_{1-6}$ alkoxy or hydroxyl. In some embodiments, $R^2$ of formula VIII is methoxy. In some embodiments, $R^2$ of formula VIII is hydroxyl. In some embodiments, $R^3$ of formula VIII is $C_{1-6}$ alkoxy. In some embodiments, $R^3$ of formula VIII is methoxy. In some embodiments, subscript m of formula VIII is 2. In some embodiments, subscript n of formula VIII is 2. In some embodiments, subscript p of formula VIII is 1. In some embodiments, subscript q of formula VIII is 0. In some embodiments, the compound of formula VIII is:

(ZINC05464492)

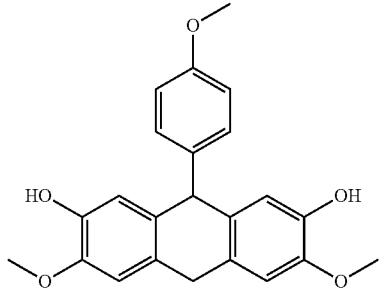

In some embodiments, the compound has the structure of formula IX:

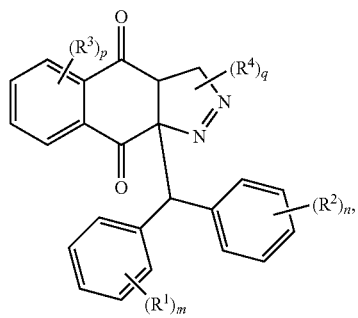

(IX)

wherein each $R^1$ is independently hydrogen, $C_{1-6}$ alkyl, $C_{1-6}$ alkoxy, halogen, hydroxyl, —$NO_2$, or —C(O)—$C_{1-6}$ alkyl. Each $R^2$ of formula IX is independently hydrogen, $C_{1-6}$ alkyl, $C_{1-6}$ alkoxy, $C_{6-12}$ aryl, hydroxyl, —CN, —$NH_2$, —C(O)O—$C_{1-6}$ alkyl, or —C(O)O$^-$. Each $R^3$ of formula IX is independently hydrogen, $C_{1-6}$ alkyl, $C_{1-6}$ alkoxy, or oxide. Each $R^4$ of formula IX is independently hydrogen or $C_{1-6}$ alkyl. The subscripts m and n of formula IX are each independently integers from 0 to 5. The subscript p of formula IX is an integer from 0 to 4. The subscript q of formula IX is an integer from 0 to 2.

In some embodiments, subscript m of formula IX is 0. In some embodiments, subscript n of formula IX is 0. In some embodiments, subscript p of formula IX is 0. In some embodiments, subscript q or formula IX is 0. In some embodiments, the compound of formula IX is:

(ZINC 05699002)

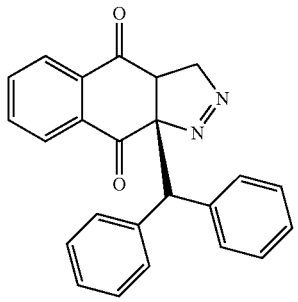

In some embodiments the compound has the structure of formula X:

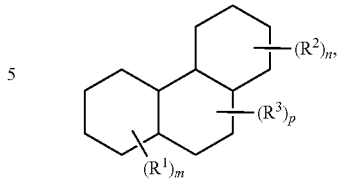

(X)

wherein each $R^1$ is independently hydrogen, $C_{1-6}$ alkyl, $C_{1-6}$ alkoxy, halogen, hydroxyl, —$NO_2$, or —C(O)—$C_{1-6}$ alkyl. Each $R^2$ of formula X is independently hydrogen, $C_{1-6}$ alkyl, $C_{1-6}$ alkoxy, $C_{6-12}$ aryl, hydroxyl, —CN, —$NH_2$, —C(O)O—$C_{1-6}$ alkyl, or —C(O)O$^-$. Each $R^3$ of formula X is independently hydrogen, $C_{1-6}$ alkyl, $C_{1-6}$ alkoxy, or oxide. The subscripts m and n of formula X are each independently integers from 0 to 5. The subscript p of formula X is an integer from 0 to 4.

In some embodiments, each $R^1$ of formula X is independently $C_{1-6}$ alkyl, $C_{1-6}$ alkylhydroxy, or hydroxyl. In some embodiments, $R^1$ of formula X is methyl. In some embodiments, $R^1$ of formula X is hydroxymethyl. In some embodiments, $R^1$ of formula X is hydroxyl. In some embodiments, each $R^2$ of formula X is independently $C_{1-6}$ alkyl. In some embodiments, $R^2$ of formula X is propyl. In some embodiments, subscript m of formula X is 3. In some embodiments, subscript n of formula X is 2. In some embodiments, the compound of formula X is:

(ZINC16889877)

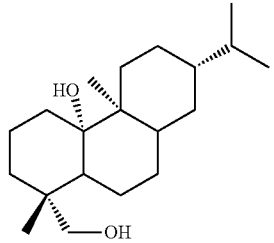

In some embodiments, the compound has the structure of formula XI:

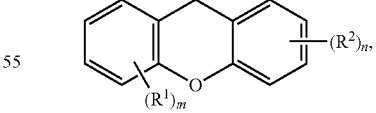

(XI)

wherein each $R^1$ is independently hydrogen, $C_{1-6}$ alkyl, $C_{1-6}$ alkoxy, halogen, hydroxyl, —$NO_2$, or —C(O)—$C_{1-6}$ alkyl. Each $R^2$ of formula XI is independently hydrogen, $C_{1-6}$ alkyl, $C_{1-6}$ alkoxy, $C_{6-12}$ aryl, hydroxyl, —CN, —$NH_2$, —C(O)O—$C_{1-6}$ alkyl, or —C(O)O$^-$. The subscripts m and n of formula XI are each independently integers from 0 to 5. The subscript w of formula XI is an integer from 0 to 3.

In some embodiments, subscript m of formula XI is 0. In some embodiments, subscript n of formula XI is 0. In some embodiments, subscript w of formula XI is 1. In some embodiments, the compound of formula XI is:

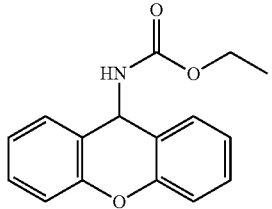
(ZINC01661542)

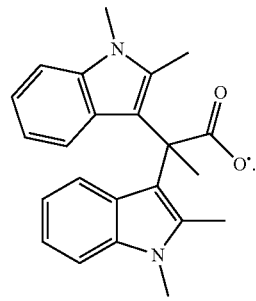
(ZINC01691943)

In some embodiments, the compound has the structure of formula XII:

In some embodiments, the compound has the structure of formula XIII:

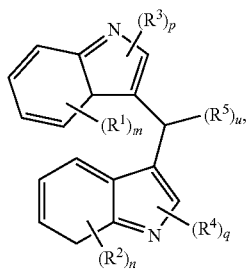
(XII)

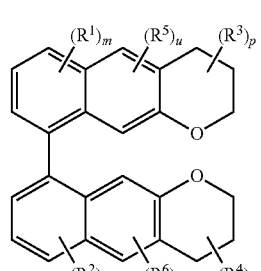
(XIII)

wherein each $R^1$ is independently hydrogen, $C_{1-6}$ alkyl, $C_{1-6}$ alkoxy, halogen, hydroxyl, —$NO_2$, or —C(O)—$C_{1-6}$ alkyl. Each $R^2$ of formula XII is independently hydrogen, $C_{1-6}$ alkyl, $C_{1-6}$ alkoxy, $C_{6-12}$ aryl, hydroxyl, —CN, —$NH_2$, —C(O)O—$C_{1-6}$ alkyl, or —C(O)O⁻. Each $R^3$ of formula XII is independently hydrogen, $C_{1-6}$ alkyl, $C_{1-6}$ alkoxy, or oxide. Each $R^4$ of formula XII is independently hydrogen or $C_{1-6}$ alkyl. Each $R^5$ of formula XII is independently hydrogen, $C_{1-6}$ alkyl, hydroxyl, or C(O)O⁻. The subscripts m and n of formula XII are each independently integers from 0 to 5. The subscript p of formula XII is an integer from 0 to 4. The subscripts q and u of formula XII are each independently integers from 0 to 2.

In some embodiments, each $R^3$ of formula XII is independently $C_{1-6}$ alkyl. In some embodiments, $R^3$ of formula XII is methyl. In some embodiments, each $R^4$ of formula XII is independently $C_{1-6}$ alkyl. In some embodiments, $R^4$ of formula XII is methyl. In some embodiments, each $R^5$ of formula XII is independently $C_{1-6}$ alkyl or —C(O)O⁻. In some embodiments, $R^5$ of formula XII is methyl. In some embodiments, $R^5$ of formula XII is —C(O)O⁻. In some embodiments, subscript m of formula XII is 0. In some embodiments, subscript n of formula n is 0. In some embodiments, subscript p of formula XII is 2. In some embodiments, subscript q of formula XII is 2. In some embodiments, subscript u of formula XII is 2. In some embodiments, the compound of formula XII is:

wherein each $R^1$ is independently hydrogen, $C_{1-6}$ alkyl, $C_{1-6}$ alkoxy, halogen, hydroxyl, —$NO_2$, or —C(O)—$C_{1-6}$ alkyl. Each $R^2$ of formula XIII is independently hydrogen, $C_{1-6}$ alkyl, $C_{1-6}$ alkoxy, $C_{6-12}$ aryl, hydroxyl, —CN, —$NH_2$, —C(O)O—$C_{1-6}$ alkyl, or —C(O)O⁻. Each $R^3$ of formula XIII is independently hydrogen, $C_{1-6}$ alkyl, $C_{1-6}$ alkoxy, or oxide. Each $R^4$ of formula XIII is independently hydrogen or $C_{1-6}$ alkyl. Each $R^5$ of formula XIII is independently hydrogen, $C_{1-6}$ alkyl, hydroxyl, or C(O)O⁻. Each $R^6$ of formula XIII is hydrogen or hydroxyl. The subscripts m and n of formula XIII are each independently integers from 0 to 5. The subscript p of formula XIII is an integer from 0 to 4. The subscripts q, u, and v of formula XIII are each independently integers from 0 to 2.

In some embodiments, $R^1$ of formula XIII is hydroxyl. In some embodiments, $R^2$ of formula XIII is hydroxyl. In some embodiments, $R^5$ of formula XIII is hydroxyl. In some embodiments, $R^6$ of formula XIII is hydroxyl. In some embodiments, each $R^3$ of formula XIII is independently $C_{1-6}$ alkyl. In some embodiments, $R^3$ of formula XIII is methyl. In some embodiments, each $R^4$ of formula XIII is independently $C_{1-6}$ alkyl. In some embodiments, $R^4$ of formula XIII is methyl. In some embodiments, subscript m of formula XIII is 2. In some embodiments, subscript n of formula XIII is 2. In some embodiments, subscript p of formula XIII is 2. In some embodiments, subscript q of formula XIII is 2. In some embodiments, subscript u of formula XIII is 1. In some embodiments, subscript v of formula XIII is 1. In some embodiments, the compound of formula XIII is:

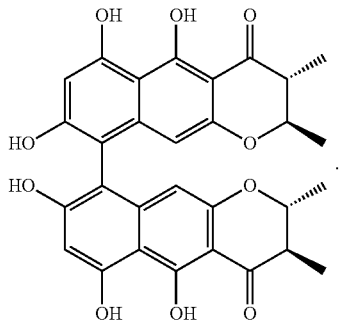

(ZINC17465983)

In some embodiments, the compound has the structure of formula XIV:

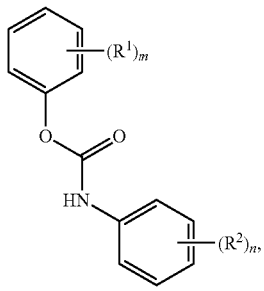

(XIV)

wherein each $R^1$ is independently hydrogen, $C_{1-6}$ alkyl, $C_{1-6}$ alkoxy, halogen, hydroxyl, —$NO_2$, or —C(O)—$C_{1-6}$ alkyl. Each $R^2$ of formula XIV is independently hydrogen, $C_{1-6}$ alkyl, $C_{1-6}$ alkoxy, $C_{6-12}$ aryl, hydroxyl, —CN, —$NH_2$, —C(O)O—$C_{1-6}$ alkyl, or —C(O)O$^-$. The subscripts m and n of formula XIV are each independently integers from 0 to 5.

In some embodiments, each $R^1$ of formula XIV is $C_{1-6}$ alkyl. In some embodiments, $R^1$ of formula XIV is butyl. In some embodiments, each $R^2$ of formula XIV is independently hydroxyl or C(O)O$^-$. In some embodiments, $R^2$ of formula XIV is hydroxyl. In some embodiments, $R^2$ of formula XIV is C(O)O$^-$. In some embodiments, subscript m of formula XIV is 1. In some embodiments, subscript n of formula XIV is 2. In some embodiments, the compound of formula XIV is:

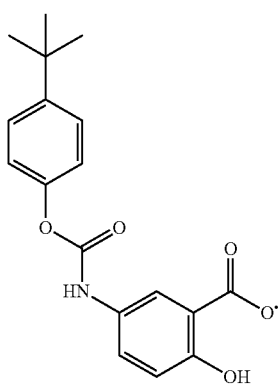

(ZINC01748097)

Figure 2:
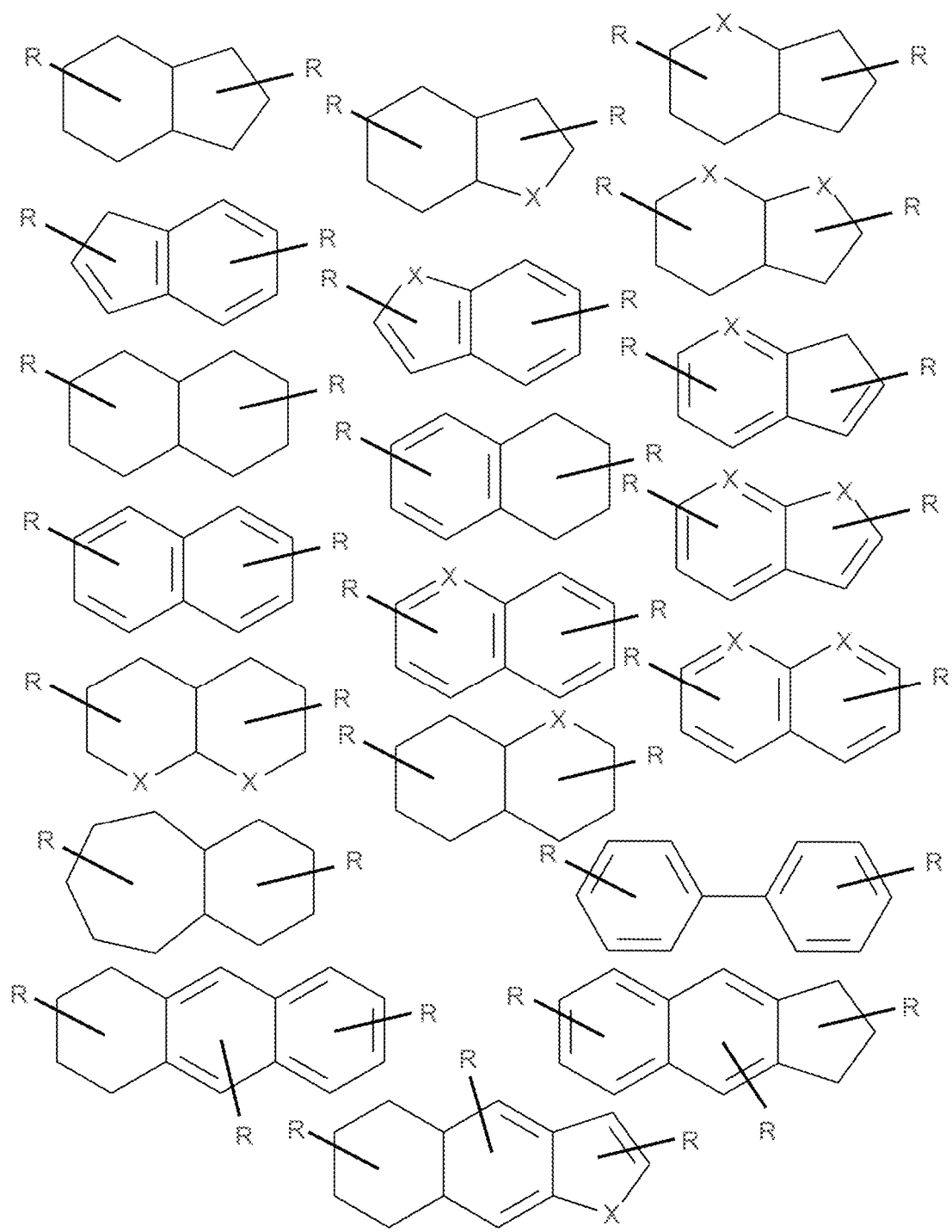
FIG. 2 presents different ligand binding motif chemical structures for NQ-site in respiratory complex III.

In some embodiments, the compound has the structure of any of the formulas of FIG. 2. Each R of FIG. 2 can independently be hydrogen, $C_{1-6}$ alkyl, $C_{1-6}$ alkylhydroxy, $C_1$-6 haloalkyl, $C_{1-6}$ alkoxy, $C_{1-6}$ haloalkoxy, $C_{6-12}$ aryl, halogen, hydroxyl, oxide, —CN, —$NH_2$, —$NO_2$, or —C(O)—$C_{1-6}$ alkyl, or —C(O)O$^-$. Each X of FIG. 2 can independently be S, N, or O.

The compounds of the present invention can also be the salts and isomers thereof. In some embodiments, the compounds of the present invention include the salt forms thereof. Examples of applicable salt forms include hydrochlorides, hydrobromides, sulfates, methanesulfonates, nitrates, maleates, acetates, citrates, fumarates, tartrates (e.g. (+)-tartrates, (−)-tartrates or mixtures thereof including racemic mixtures), succinates, benzoates and salts with amino acids such as glutamic acid. These salts may be prepared by methods known to those skilled in art. When compounds of the present invention contain relatively basic functionalities, acid addition salts can be obtained by contacting the neutral form of such compounds with a sufficient amount of the desired acid, either neat or in a suitable inert solvent. Examples of acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge et al. (1977) *Journal of Pharmaceutical Science* 66:1). Certain specific compounds of the present invention contain basic acidic functionalities that allow the compounds to be converted into base addition salts. Additional information on suitable pharmaceutically acceptable salts can be found in Remington's Pharmaceutical Sciences, 17th ed., Mack Publishing Company, Easton, Pa., 1985, which is incorporated herein by reference.

The neutral forms of the compounds are preferably regenerated by contacting the salt with a base or acid and isolating the parent compound in the conventional manner. The parent form of the compound differs from the various salt forms in certain physical properties, such as solubility in polar solvents.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the scope of the present invention. The compounds of the present invention do not include those which are known in art to be too unstable to synthesize and/or isolate. The present invention is meant to include compounds in racemic and optically pure forms. Optically active (R)- and (S)-, or (D)- and (L)-isomers may be prepared using chiral synthons or chiral reagents, or resolved using conventional techniques.

Isomers include compounds having the same number and kind of atoms, and hence the same molecular weight, but differing in respect to the structural arrangement or configuration of the atoms.

It will be apparent to one skilled in the art that certain compounds of this invention may exist in tautomeric forms, all such tautomeric forms of the compounds being within the scope of the invention. Tautomer refers to one of two or more structural isomers which exist in equilibrium and which are readily converted from one isomeric form to another.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention.

Unless otherwise stated, the compounds of the present invention may also contain unnatural proportions of atomic isotopes at one or more of the atoms that constitute such compounds. For example, the compounds of the present invention may be radiolabeled with radioactive isotopes, such as for example deuterium ($^2$H), tritium ($^3$H), iodine-125 ($^{125}$I), carbon-13 ($^{13}$C), or carbon-14 ($^{14}$C). All isotopic variations of the compounds of the present invention, whether radioactive or not, are encompassed within the scope of the present invention.

In addition to salt forms, the present invention provides compounds, which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

IV. Methods for Treatment

In one aspect, the present invention provides several methods for treatment of cancer in a subject. The methods include administering to a subject in need of such treatment, a therapeutically effective amount of a compound having the structure:

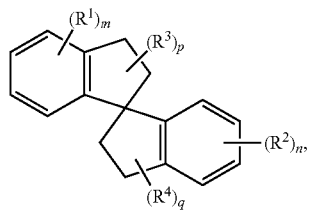

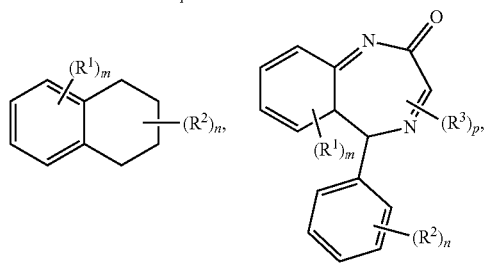

-continued

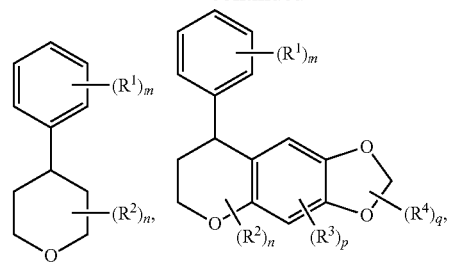

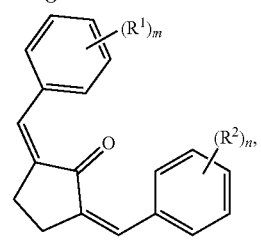

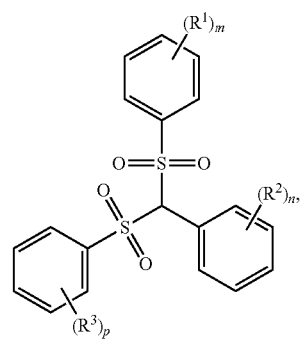

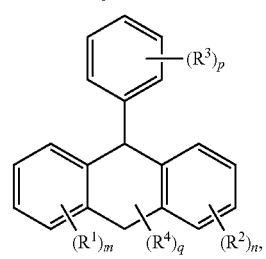

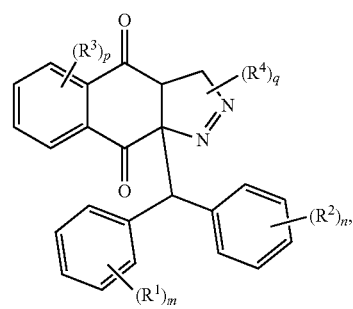

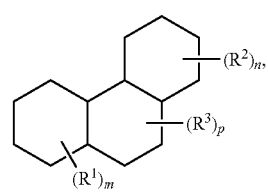

-continued

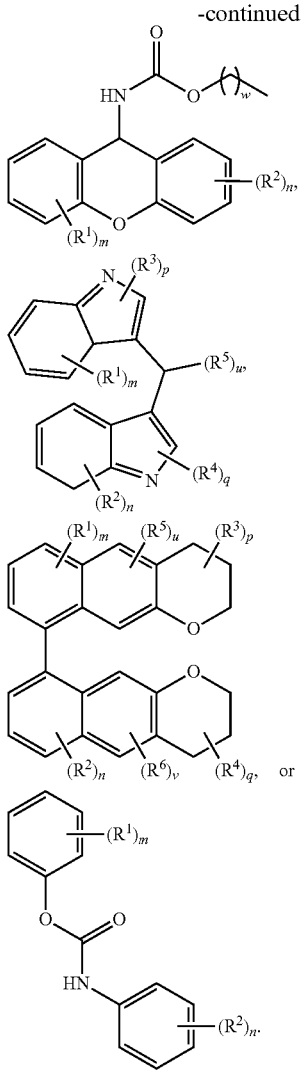

Each $R^1$, $R^2$, $R^3$, $R^4$, $R^5$, and $R^6$ can independently be hydrogen, $C_{1-6}$ alkyl, $C_{1-6}$ alkylhydroxy, $C_{1-6}$ haloalkyl, $C_{1-6}$ alkoxy, $C_{1-6}$ haloalkoxy, $C_{6-12}$ aryl, halogen, hydroxyl, oxide, —CN, —$NH_2$, —$NO_2$, and —C(O)—$C_{1-6}$ alkyl, or —C(O)O$^-$. The subscripts m and n can each independently be integers from 0 to 5. The subscript p is an integer from 0 to 4. The subscripts q, u, and v can each independently be integers from 0 to 2. The subscript w is an integer from 0 to 3.

In some embodiments, the compound administered for treatment has any one of the structures of formulas I-XIV described above. In some embodiments, more than one compound is administered for treatment. In some embodiments, the more than one administered compounds include two or more compounds each having a structure of one of formulas I-XIV described above.

In some embodiments, the subject is a patient suffering from cancer. In some embodiments, the patient is a human. In some embodiments, the patient suffers from more than one cancer. Examples of cancers suitable for treatment with the present invention include, but are not limited to, acute lymphoblastic leukemia, acute myeloid leukemia, adrenocortical carcinoma, anal cancer, appendix cancer, astrocytoma, basal-cell carcinoma, bile duct cancer, bladder cancer, bone tumor, brainstem glioma, brain cancer, cerebellar astrocytoma, cerebral astrocytoma, ependymoma, medulloblastoma, supratentorial primitive neuroectodermal tumors, visual pathway and hypothalamic glioma, breast cancer, bronchial adenomas, Burkitt's lymphoma, central nervous system lymphoma, cerebellar astrocytoma, cervical cancer, chondrosarcoma, chronic lymphocytic leukemia, chronic myelogenous leukemia, chronic myeloproliferative disorders, colon cancer, cutaneous T-cell lymphoma, desmoplastic small round cell tumor, endometrial cancer, ependymoma, epitheliod hemangioendothelioma (EHE), esophageal cancer, Ewing's sarcoma, extracranial germ cell tumor, extragonadal germ cell tumor, extrahepatic bile duct cancer, eye cancer, intraocular melanoma, retinoblastoma, gallbladder cancer, gastric cancer, gastrointestinal carcinoid tumor, gastrointestinal stromal tumor (GIST), germ cell tumor, gestational trophoblastic tumor, gastric carcinoid, hairy cell leukemia, head and neck cancer, heart cancer, hepatocellular cancer, Hodgkin lymphoma, hypopharyngeal cancer, hypothalamic and visual pathway glioma, childhood, intraocular melanoma, islet cell carcinoma, Kaposi sarcoma, kidney cancer, laryngeal cancer, leukaemias, lip and oral cavity cancer, liposarcoma, liver cancer, non-small cell lung cancer, small-cell lung cancer, lymphomas, macroglobulinemia, male breast cancer, malignant fibrous histiocytoma of bone, medulloblastoma, melanoma, Merkel cell cancer, mesothelioma, metastatic squamous neck cancer, mouth cancer, multiple endocrine neoplasia syndrome, multiple myeloma, mycosis fungoides, myelodysplastic syndromes, myelogenous leukemia, myeloid leukemia, adult acute, myeloproliferative disorders, chronic, myxoma, nasal cavity and paranasal sinus cancer, nasopharyngeal carcinoma, neuroblastoma, non-Hodgkin lymphoma, oligodendroglioma, oral cancer, oropharyngeal cancer, osteosarcoma, ovarian cancer, ovarian epithelial cancer, ovarian germ cell tumor, ovarian low malignant potential tumor, pancreatic cancer, paranasal sinus and nasal cavity cancer, parathyroid cancer, penile cancer, pharyngeal cancer, pheochromocytoma, pineal astrocytoma, pineal germinoma, pineoblastoma, supratentorial primitive neuroectodermal tumors, pituitary adenoma. plasma cell neoplasia, pleuropulmonary blastoma, primary central nervous system lymphoma, prostate cancer, rectal cancer, renal cell carcinoma, retinoblastoma, rhabdomyosarcoma, salivary gland cancer, Ewing sarcoma, Kaposi sarcoma, soft tissue sarcoma, uterine sarcoma, Sezary syndrome, non-melanoma skin cancer, melanoma Merkel cell skin carcinoma, small intestine cancer, squamous cell carcinoma, squamous neck cancer, stomach cancer, cutaneous T-Cell lymphoma, testicular cancer, throat cancer, thymoma, thyroid cancer, transitional cell cancer of the renal pelvis and ureter, trophoblastic tumor, gestational, urethral cancer, uterine cancer, vaginal cancer, vulvar cancer, Waldenstrom macroglobulinemia, and Wilms tumor.

The compounds and compositions of the present invention can be delivered by any suitable means, including oral, parenteral and topical methods. Transdermal administration methods, by a topical route, can be formulated as applicator sticks, solutions, suspensions, emulsions, gels, creams, ointments, pastes, jellies, paints, powders, and aerosols.

The pharmaceutical preparation is preferably in unit dosage form. In such form the preparation is subdivided into unit doses containing appropriate quantities of the compounds and compositions of the present invention. The unit dosage form can be a packaged preparation, the package containing discrete quantities of preparation, such as packeted tablets, capsules, and powders in vials or ampoules.

Also, the unit dosage form can be a capsule, tablet, cachet, or lozenge itself, or it can be the appropriate number of any of these in packaged form.

The compounds and compositions of the present invention can be co-administered with other agents. Co-administration includes administering the compound or composition of the present invention within 0.5, 1, 2, 4, 6, 8, 10, 12, 16, 20, or 24 hours of the other agent. Co-administration also includes administering simultaneously, approximately simultaneously (e.g., within about 1, 5, 10, 15, 20, or 30 minutes of each other), or sequentially in any order. Moreover, the compounds and compositions of the present invention can each be administered once a day, or two, three, or more times per day so as to provide the preferred dosage level per day.

In some embodiments, co-administration can be accomplished by co-formulation, i.e., preparing a single pharmaceutical composition including the compounds and compositions of the present invention and any other agent. Alternatively, the various components can be formulated separately.

The compounds and compositions of the present invention, and any other agents, can be present in any suitable amount, and can depend on various factors including, but not limited to, weight and age of the subject, state of the disease, etc. Suitable dosage ranges include from about 0.1 mg to about 10,000 mg, or about 1 mg to about 1000 mg, or about 10 mg to about 750 mg, or about 25 mg to about 500 mg, or about 50 mg to about 250 mg. Suitable dosages also include about 1 mg, 5, 10, 20, 30, 40, 50, 60, 70, 80, 90, 100, 200, 300, 400, 500, 600, 700, 800, 900 or 1000 mg.

The compounds of the present invention can be administered at any suitable frequency, interval and duration. For example, the compound of the present invention can be administered once an hour, or two, three or more times an hour, once a day, or two, three, or more times per day, or once every 2, 3, 4, 5, 6, or 7 days, so as to provide the preferred dosage level. When the compound of the present invention is administered more than once a day, representative intervals include 5, 10, 15, 20, 30, 45 and 60 minutes, as well as 1, 2, 4, 6, 8, 10, 12, 16, 20, and 24 hours. The compound of the present invention can be administered once, twice, or three or more times, for an hour, for 1 to 6 hours, for 1 to 12 hours, for 1 to 24 hours, for 6 to 12 hours, for 12 to 24 hours, for a single day, for 1 to 7 days, for a single week, for 1 to 4 weeks, for a month, for 1 to 12 months, for a year or more, or even indefinitely.

V. Pharmaceutical Compositions

In some embodiments, the present invention provides a pharmaceutical composition including a pharmaceutically acceptable excipient and a compound of the present invention. In some embodiments, the composition also includes an additional chemotherapeutic agent.

Chemotherapeutic Agents

Chemotherapeutic agents suitable for use with the present invention include those agents that are useful for treating or ameliorating cancer and include, but are not limited to, aldesleukin, alectinib anaplastic lymphoma kinase, cabozantinib, elotuzumab, fluoxymesterone, iobenguane, imiquimod, interferon, ixazomib, lanreotide, lentinan, mitotane, nab-paclitaxel, necitumumab, octreotide, somatostatin, omacetaxine, sipuleucel-T, tegafur/gimeracil/oteracil and tegafur/uracil.

Additional chemotherapeutic agents suitable for use with the present invention include, but are not limited to, azacitidine, capecitabine, carmofur, cladribine, clofarabine, cytarabine, decitabine, floxuridine, fludarabine, fluorouracil, gemcitabine, mercaptopurine, nelarabine, pentostatin, tegafur, tioguanine, trifluridine/tipiracil, methotrexate, pemetrexed, pralatrexate, raltitrexed, hydroxycarbamide, irinotecan, topotecan, daunorubicin, doxorubicin, epirubicin, idarubicin, mitoxantrone, valrubicin, etoposide, teniposide, cabazitaxel, docetaxel, paclitaxel, vinblastine, vincristine, vindesine, vinflunine, vinorelbine, bendamustine, busulfan, carmustine, chlorambucil, chlormethine, cyclophosphamide, dacarbazine, fotemustine, ifosfamide, lomustine, melphalan, streptozotocin, temozolomide, trabectedin, carboplatin, cisplatin, nedaplatin, oxaliplatin, altretamine, bleomycin, bortezomib, carfilzomib, dactinomycin, eribulin, estramustine, ixabepilone, mitomycin, procarbazine, abarelix, abiraterone, anastrozole, bicalutamide, cyproterone, degarelix, enzalutamide, exemestane, flutamide, fulvestrant, goserelin, histrelin, letrozole, leuprolide, mifepristone, nilutamide, tamoxifen, toremifene, triptorelin, ibritumomab tiuxetan, radium Ra 223 dichloride, strontium-89, samarium (153 Sm) lexidronam, tositumomab, ado-trastuzumab emtansine, alemtuzumab, bevacizumab, blinatumomab, brentuximab vedotin, cetuximab, daratumumab, denosumab, dinutuximab, gemtuzumab ozogamicin, ibritumomab tiuxetan, ipilimumab, nivolumab, obinutuzumab, ofatumumab, panitumumab, pembrolizumab, pertuzumab, ramucirumab, rituximab, tositumomab, trastuzumab, afatinib, aflibercept, axitinib, bosutinib, cobimetinib, crizotinib, dasatinib, erlotinib, gefitinib, imatinibl, lapatinibl, lenvatinibl, nilotinib, osimertinib, pazopanib, ponatinib, regorafenib, ruxolitinib, sorafenib, sunitinib, trametinib, vandetanib, everolimus, temsirolimus, alitretinoin, bexarotene, isotretinoin, tamibarotene, tretinoin, lenalidomide, pomalidomide, thalidomide, belinostat, panobinostat, romidepsin, valproate, vorinostat, anagrelide, arsenic trioxide, asparaginase, *Bacillus* Calmete-Guérin vaccine, ceritinib, dabrafenib, denileukin diftitox, idelalisib, ibrutinib, olaparib, palbociclib, sonidegib, talimogene laherparepvec, vemurafenib, and vismodegib.

The chemotherapeutic agents of the present invention also include the salts, hydrates, solvates and prodrug forms. The compounds of the present invention also include the isomers and metabolites of those described above.

Salts include, but are not limited to, sulfate, citrate, acetate, oxalate, chloride, bromide, iodide, nitrate, bisulfate, phosphate, acid phosphate, phosphonic acid, isonicotinate, lactate, salicylate, citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate, and pamoate (i.e., 1,1'-methylene-bis-(2-hydroxy-3-naphthoate)) salts. Other salts include, but are not limited to, salts with inorganic bases including alkali metal salts such as sodium salts, and potassium salts; alkaline earth metal salts such as calcium salts, and magnesium salts; aluminum salts; and ammonium salts. Other salts with organic bases include salts with diethylamine, diethanolamine, meglumine, and N,N'-dibenzylethylenediamine.

The neutral forms of the chemotherapeutic agents can be regenerated by contacting the salt with a base or acid and isolating the parent anti-inflammatory glucocorticosteroid in the conventional manner. The parent form of the anti-inflammatory glucocorticosteroid differs from the various salt forms in certain physical properties, such as solubility in polar solvents, but otherwise the salts are equivalent to the parent form of the compound for the purposes of the present invention.

Certain chemotherapeutic agents of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain chemotherapeutic agents of the present invention possess asymmetric carbon atoms (optical centers) or double bonds; the enantiomers, racemates, diastereomers, tautomers, geometric isomers, stereoisomeric forms that may be defined, in terms of absolute stereochemistry, as (R)- or (S)- or, as (D)- or (L)- for amino acids, and individual isomers are encompassed within the scope of the present invention. The compounds of the present invention do not include those which are known in art to be too unstable to synthesize and/or isolate. The present invention is meant to include compounds in racemic and optically pure forms. Optically active (R)- and (S)-, or (D)- and (L)-isomers may be prepared using chiral synthons or chiral reagents, or resolved using conventional techniques.

The present invention also provides chemotherapeutic agents which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

VI. Formulations

The compositions of the present invention can be prepared in a wide variety of oral, parenteral and topical dosage forms. Oral preparations include tablets, pills, powder, dragees, capsules, liquids, lozenges, cachets, gels, syrups, slurries, suspensions, etc., suitable for ingestion by the patient. The compositions of the present invention can also be administered by injection, that is, intravenously, intramuscularly, intracutaneously, subcutaneously, intraduodenally, or intraperitoneally. Also, the compositions described herein can be administered by inhalation, for example, intranasally. Additionally, the compositions of the present invention can be administered transdermally. The compositions of this invention can also be administered by intraocular, intravaginal, and intrarectal routes including suppositories, insufflation, powders and aerosol formulations (for examples of steroid inhalants, see Rohatagi (1995) *J Clin. Pharmacol.* 35:1187; and Tjwa (1995) *Ann. Allergy Asthma Immunol.* 75:107). Accordingly, the present invention also provides pharmaceutical compositions including a pharmaceutically acceptable carrier or excipient and a compound of the present invention.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances, which may also act as diluents, flavoring agents, binders, preservatives, tablet disintegrating agents, or an encapsulating material. Details on techniques for formulation and administration are well described in the scientific and patent literature, see, e.g., the latest edition of Remington's Pharmaceutical Sciences, Maack Publishing Co, Easton Pa. ("Remington's").

In powders, the carrier is a finely divided solid, which is in a mixture with the finely divided active component. In tablets, the active component is mixed with the carrier having the necessary binding properties in suitable proportions and compacted in the shape and size desired. The powders and tablets preferably contain from 5% or 10% to 70% of the compounds of the present invention.

Suitable solid excipients include, but are not limited to, magnesium carbonate; magnesium stearate; talc; pectin; dextrin; starch; tragacanth; a low melting wax; cocoa butter; carbohydrates; sugars including, but not limited to, lactose, sucrose, mannitol, or sorbitol, starch from corn, wheat, rice, potato, or other plants; cellulose such as methyl cellulose, hydroxypropylmethyl-cellulose, or sodium carboxymethylcellulose; and gums including arabic and tragacanth; as well as proteins including, but not limited to, gelatin and collagen. If desired, disintegrating or solubilizing agents may be added, such as the cross-linked polyvinyl pyrrolidone, agar, alginic acid, or a salt thereof, such as sodium alginate.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound (i.e., dosage). Pharmaceutical preparations of the invention can also be used orally using, for example, push-fit capsules made of gelatin, as well as soft, sealed capsules made of gelatin and a coating such as glycerol or sorbitol. Push-fit capsules can contain the compounds of the present invention mixed with a filler or binders such as lactose or starches, lubricants such as talc or magnesium stearate, and, optionally, stabilizers. In soft capsules, the compounds of the present invention may be dissolved or suspended in suitable liquids, such as fatty oils, liquid paraffin, or liquid polyethylene glycol with or without stabilizers.

For preparing suppositories, a low melting wax, such as a mixture of fatty acid glycerides or cocoa butter, is first melted and the compounds of the present invention are dispersed homogeneously therein, as by stirring. The molten homogeneous mixture is then poured into convenient sized molds, allowed to cool, and thereby to solidify.

Liquid form preparations include solutions, suspensions, and emulsions, for example, water or water/propylene glycol solutions. For parenteral injection, liquid preparations can be formulated in solution in aqueous polyethylene glycol solution.

Aqueous solutions suitable for oral use can be prepared by dissolving the compounds of the present invention in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, hydroxypropylmethylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan mono-oleate). The aqueous suspension can also contain one or more preservatives such as ethyl or n-propyl p-hydroxybenzoate, one or more coloring agents, one or more flavoring agents and one or more sweetening agents, such as sucrose, aspartame or saccharin. Formulations can be adjusted for osmolarity.

Also included are solid form preparations, which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

Oil suspensions can be formulated by suspending the compounds of the present invention in a vegetable oil, such as arachis oil, olive oil, sesame oil or coconut oil, or in a mineral oil such as liquid paraffin; or a mixture of these. The oil suspensions can contain a thickening agent, such as beeswax, hard paraffin or cetyl alcohol. Sweetening agents can be added to provide a palatable oral preparation, such as glycerol, sorbitol or sucrose. These formulations can be preserved by the addition of an antioxidant such as ascorbic acid. As an example of an injectable oil vehicle, see Minto (1997) *J. Pharmacol. Exp. Ther.* 281:93. The pharmaceutical formulations of the invention can also be in the form of oil-in-water emulsions. The oily phase can be a vegetable oil or a mineral oil, described above, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsion can also contain sweetening agents and flavoring agents, as in the formulation of syrups and elixirs. Such formulations can also contain a demulcent, a preservative, or a coloring agent.

The compositions of the present invention can also be delivered as microspheres for slow release in the body. For example, microspheres can be formulated for administration via intradermal injection of drug-containing microspheres, which slowly release subcutaneously (see Rao (1995) *J. Biomater. Sci. Polym.* Ed. 7:623); as biodegradable and injectable gel formulations (see, e.g., Gao (1995) *Pharm. Res.* 12:857); or, as microspheres for oral administration (see, e.g., Eyles (1997) *J. Pharm. Pharmacol.* 49:669). Both transdermal and intradermal routes afford constant delivery for weeks or months.

In another embodiment, the compositions of the present invention can be formulated for parenteral administration, such as intravenous (IV) administration or administration into a body cavity or lumen of an organ. The formulations for administration will commonly comprise a solution of the compositions of the present invention dissolved in a pharmaceutically acceptable carrier. Among the acceptable vehicles and solvents that can be employed are water and Ringer's solution, an isotonic sodium chloride. In addition, sterile fixed oils can conventionally be employed as a solvent or suspending medium. For this purpose any bland fixed oil can be employed including synthetic mono- or diglycerides. In addition, fatty acids such as oleic acid can likewise be used in the preparation of injectables. These solutions are sterile and generally free of undesirable matter. These formulations may be sterilized by conventional, well known sterilization techniques. The formulations may contain pharmaceutically acceptable auxiliary substances as required to approximate physiological conditions such as pH adjusting and buffering agents, toxicity adjusting agents, e.g., sodium acetate, sodium chloride, potassium chloride, calcium chloride, sodium lactate and the like. The concentration of the compositions of the present invention in these formulations can vary widely, and will be selected primarily based on fluid volumes, viscosities, body weight, and the like, in accordance with the particular mode of administration selected and the patient's needs. For IV administration, the formulation can be a sterile injectable preparation, such as a sterile injectable aqueous or oleaginous suspension. This suspension can be formulated according to the known art using those suitable dispersing or wetting agents and suspending agents. The sterile injectable preparation can also be a sterile injectable solution or suspension in a nontoxic parenterally-acceptable diluent or solvent, such as a solution of 1,3-butanediol.

In another embodiment, the formulations of the compositions of the present invention can be delivered by the use of liposomes which fuse with the cellular membrane or are endocytosed, i.e., by employing ligands attached to the liposome, or attached directly to the oligonucleotide, that bind to surface membrane protein receptors of the cell resulting in endocytosis. By using liposomes, particularly where the liposome surface carries ligands specific for target cells, or are otherwise preferentially directed to a specific organ, one can focus the delivery of the compositions of the present invention into the target cells in vivo. (See, e.g., Al-Muhammed (1996) *J. Microencapsul.* 13:293; Chonn (1995) *Curr. Opin. Biotechnol.* 6:698; and Ostro (1989) *Am. J. Hosp. Pharm.* 46:1576).

Lipid-based drug delivery systems include lipid solutions, lipid emulsions, lipid dispersions, self-emulsifying drug delivery systems (SEDDS) and self-microemulsifying drug delivery systems (SMEDDS). In particular, SEDDS and SMEDDS are isotropic mixtures of lipids, surfactants and co-surfactants that can disperse spontaneously in aqueous media and form fine emulsions (SEDDS) or microemulsions (SMEDDS). Lipids useful in the formulations of the present invention include any natural or synthetic lipids including, but not limited to, sesame seed oil, olive oil, castor oil, peanut oil, fatty acid esters, glycerol esters, Labrafil®, Labrasol®, Cremophor®, Solutol®, Tween®, Capryol®, Capmul®, Captex®, and Peceol®.

In another embodiment, the formulations of the compositions of the present invention can be delivered by the use of nanoparticles. For example, the use of spin-labeled fluorophores is discussed in Li et al. (2012) *ACS Nano.* 6:9485. Nanoparticles have emerged as a major class of vehicles to deliver conventional anticancer drugs. Nanoparticle drug delivery systems offer several distinct advantages, such as controlled release and prolonged circulation time, as well as passive and active tumor targeting (Cabral et al. (2011) *Nat. Nanotechnol.* 6:815; Gref et al. (1994) *Science* 263:1600; Liu and Allen (2006) *Curr. Pharm.* 12:4685; and Li et al. (2009) *Nanotechnology* 20:065104). In some embodiments, the compound is hydrophobic and can be easily loaded inside a nanomicelle. The nanomicelle can comprise noncrosslinked micellar nanoparticles (NCMN). The nanomicelle can comprise disulfide-crosslinked micellar nanoparticles (DCMN).

In some embodiments, the formulations of the compositions of the present invention comprise solubility aids. The solubility aid can be, for example, a cyclodextrin. The use of cyclodextrins as solubility aids for highly water-insoluble steroids is discussed in U.S. Patent Application Publication Nos. US 2015/0018327 and US 2015/0313915. The cyclodextrin can be, for example, a β-cyclodextrin. In some embodiments, the cyclodextrin is a sulfo butyl ether β-cyclodextrin.

VII. Examples

The following examples are offered to illustrate, but not to limit, the claimed invention.

Example 1. Preliminary in Silico Screen of Ligand Binding to the NQ-Site of Respiratory Complex III A series of virtual screening computations was conducted with 1957 ligands retrieved from the ZINC database which is freely available from the Shoichet Laboratory at the University of California, San Francisco (http://zinc.docking.org/; Irwin and Shiochet (2005) *J. Chem. Inf. Model* 45:177). The subset was processed further by AutoDock-Tools utility (prepareligand4.py; Forli et al. (2016) *Nature Protocols* 11:905) to add any missing polar hydrogens while preserving the original partial charges and to convert from Syby1 mol2 format to Autodock PDBQT format.

Virtual screening calculations were carried out using PyRx0.9.2 (Dallakyan et al. (2015) *Methods Mol. Biol.* 1263:243) utilizing both Lamarckian Genetic algorithm (LG) search method in Autodock 4.2 and Autodock Vina 4.2 advanced gradient optimization search method which was proved to be more accurate than Autodock (Trott and Olson (2010) 1 *Comput. Chem.* 31:455). Default settings were used for Autodock Vina. For Autodock LG search method, we used the default settings except for the following docking parameters of 100 for ga_run, 10,000,000 for ga_num_evals and 1.5 for tstep.

Each of the candidate ligands from the docking calculations was into the novel NQ-site of the previously energy-minimized $bc_1$ structure (PDB ID: 1BE3). Ligand insertion was accomplished by structural superposition of the docked cytochrome b chain (with the ligand) and the energy-minimized $bc_1$ structure using the Chimera program (Pettersen et al. (2004) *J. Comput. Chem.* 25:1605) and the default settings for Needleman-Wunsch algorithm with BLOSUM-62. Subsequently, the whole system was energy minimized using CHARMM PARAM36 (Klauda et al. (2010) *J. Phys. Chem. B* 114:7830) force field for 300,000 steps with periodic boundary condition and then equilibrated for 100 ps. Molecular dynamics simulation was run on the whole system for 50 nanoseconds. Parameterization of the different discovered ligands were calculated using SwissParam tool (www.swissparam.ch; Zoete et al. (2011) *J. Comput. Chem.* 32:2359). Intermolecular interaction energies of the different ligands were computed based on MM-PBSA free-energy calculation method using the GROMACS g_mmpbsa tool (Kumari et al. (2014) 54:1951) where different energy terms (electrostatic energy $E_{elec}$, van-der Waals energy $E_{vdw}$ and non-electrostatic solvation energy using the solvent-accessible surface area $E_{SASA}$) were computed based on the force field parameters. Polar solvation energy ($E_{polar}$) was calculated using the Adaptive Poission-Boltzmann Solver (APBS) tool (www.poissonboltzman-n.org; Baker et al. (2001) *Proc. Natl. Acad. Sci.* 107:19157).

Figure 3:
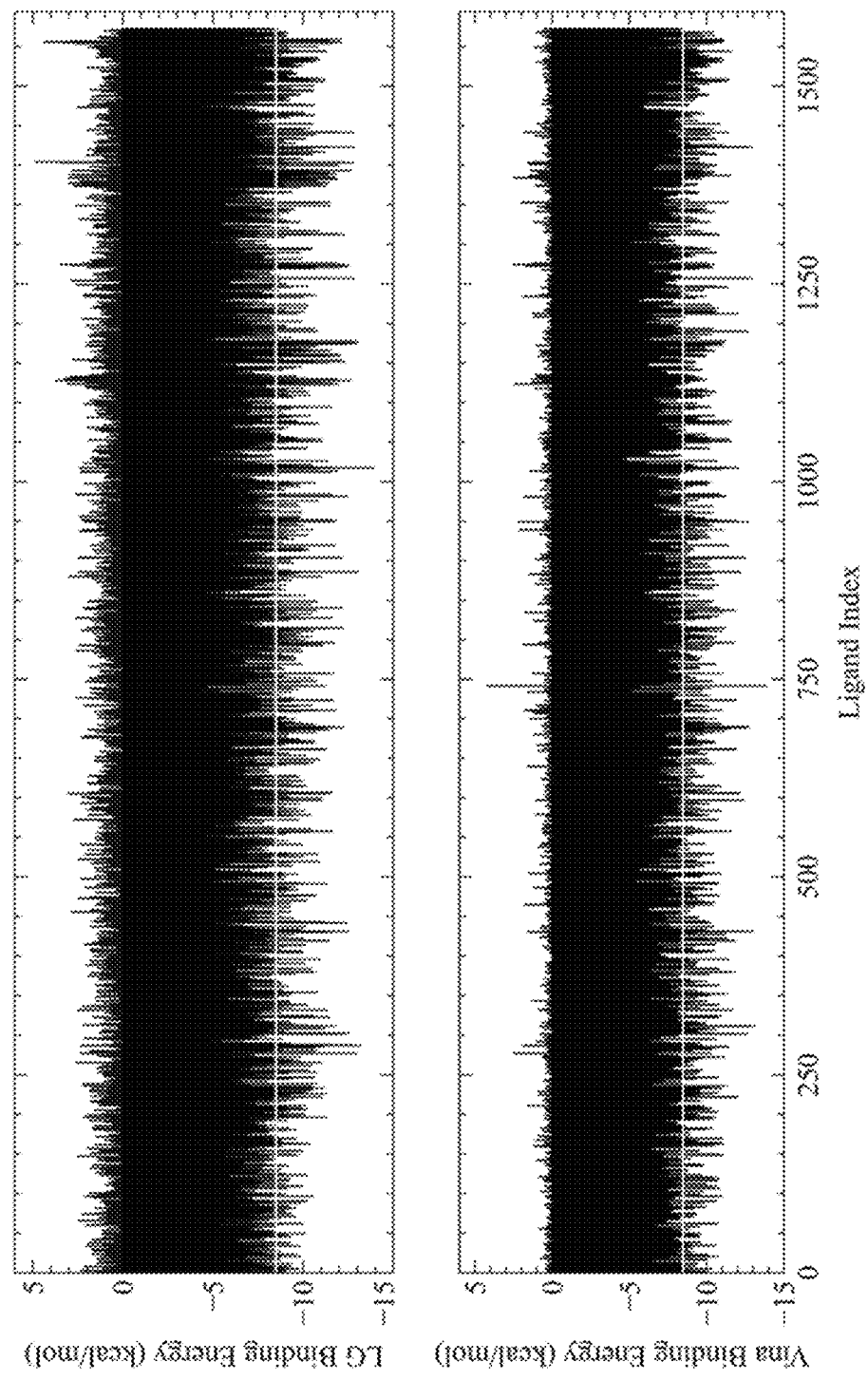
FIG. 3 is a graph of docking results of the preliminary ligand set at the NQ-site using fixed residues against flexible residues. The positive difference of the binding energies (fixed-flexible) is plotted at the top. White lines represent the cut-off binding energy of $QH_2$ molecule at NQ site.

To account for flexibility of the NQ-binding site and the different possible conformations of the Phe90 residue, we performed the docking calculation using both fixed and flexible residues (Phe90, Phe91, Ile92, Leu94 and Tyr95) as shown in FIG. 3. From the data shown in FIG. 3, only 39 ligands show a preferential binding by at least 1 kcal/mol at NQ-site in the flexible-residues docking mode compared to the fixed mode in both docking search algorithms. In this way it was ensured that those picked ligands adjust the NQ-site residues and hence bind more firmly. Such modification of the NQ-site residues is desirable because it affects the Phe90 internal switch orientation, which is our ultimate target. The influence of those picked ligands on the orientation of Phe90 was subsequently investigated, and those ligands were chosen which orient Phe90 residue away from the intra-heme b region. In addition, docking calculations were performed of the $QH_2$ at NQ-site as above (indicated by white line in FIG. 3) to exclude the ligands that have flexible-mode binding energy higher than that of the $QH_2$ molecule at the NQ-site (which is on average around −8.75 kcal/mol) in either Vina or LG search methods. The result was 30 ligands which have both preferential binding at the NQ-site compared to $QH_2$ molecule and induce the desired conformational change of Phe90 residue.

Figure 4:
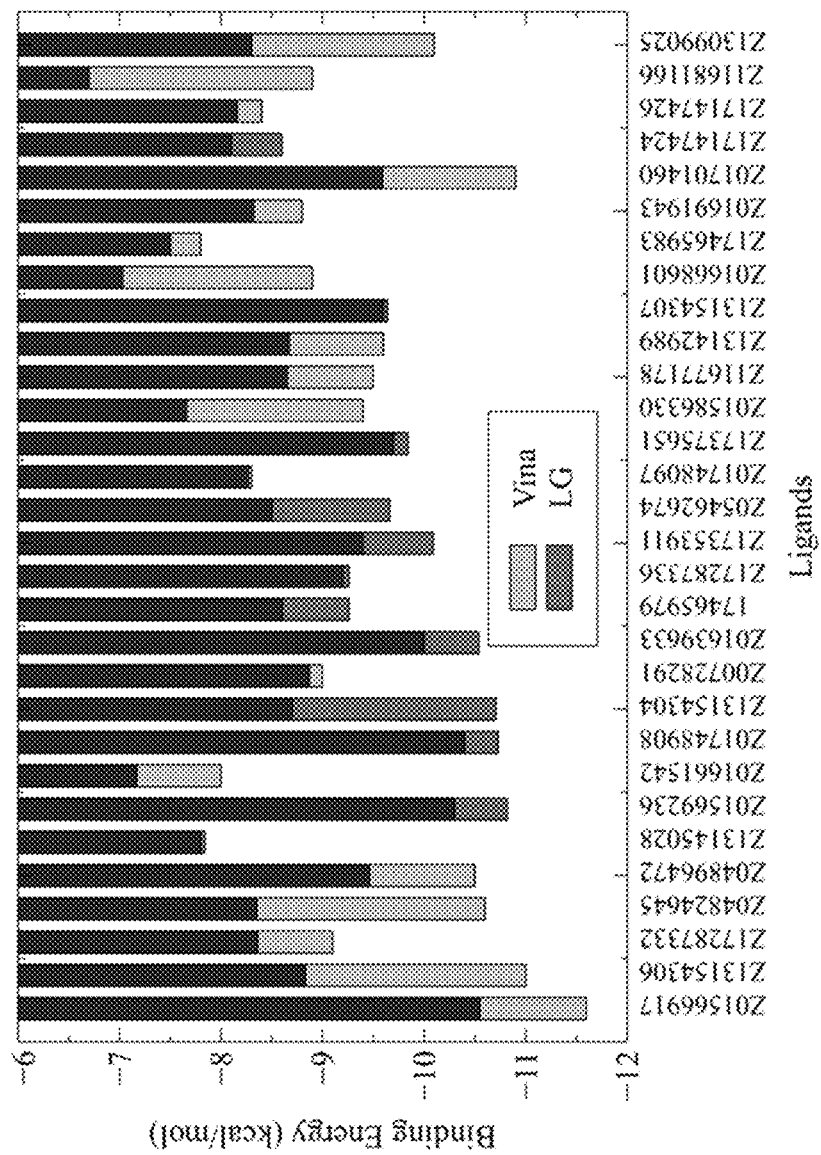
FIG. 4 is a graph of docking results at $Q_o$ site (1NTZ in PDB) of the selected 30 ligands from FIG. 3 using Vina (light grey bars) and LG (dark grey bars) search algorithms. Black bars represent the overlap between Vina and LG corresponding bars.
Figure 5:
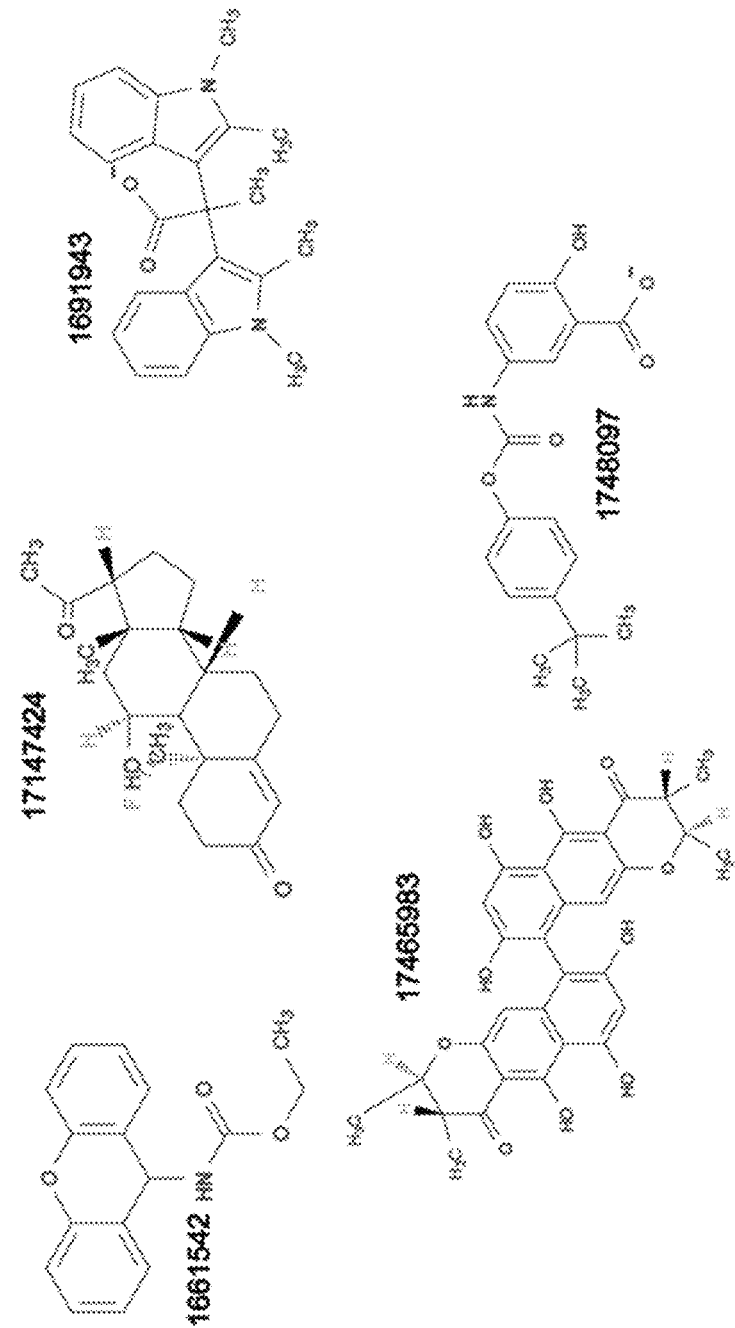
FIG. 5 shows chemical structures of five candidate ligands.

The ligand search was further restricted such that the candidate ligands would not compete with $QH_2$ molecule for binding at $Q_o$ site. This is to minimize any possible inhibition of the enzyme by those ligands so as to retain heme $b_L$ reduction by $QH_2$, while at the same time shutting down heme $b_L$ to heme $b_H$ electron transfer and hence allowing for ROS production. Further docking analysis of the resultant 30 ligands into the active $Q_o$ site (as it exists in PDB 1NTZ) reduced the number of ligands down to 6 candidates. As shown in FIG. 4 and listed in Table 1, those 6 candidate ligands exhibit binding energy lower than 8.8 kcal/mol and hence would bind preferentially at NQ-site, but not at $Q_o$ site. The chemical structures of those ligands are shown in FIG. 5.

TABLE 1

Vina and Lamarkian Genetic docking results for the 6 candidate ligands and QH2 molecule at NQ and Qo sites.

| | Binding Energy at NQ Site (kcal/mol) | | | | Binding Energy at $Q_o$ Site (kcal/mol) | |
|---|---|---|---|---|---|---|
| | Vina Method | | LG Method | | Vina Method | LG Method |
| Ligand | Fix | Flex | Fix | Flex | | |
| ZINC01661542 | −8.6 | −10.4 | −7.2 | −8.7 | −8.0 | −7.2 |
| ZINC01691943 | −7.6 | −8.7 | −8.3 | −9.4 | −8.8 | −8.3 |
| ZINC01748097 | −8.7 | −10.1 | −8.3 | −9.8 | −8.3 | −8.3 |
| ZINC17465983 | −8.3 | −9.5 | −7.5 | −12.4 | −7.8 | −7.5 |
| ZINC17147424 | −7.5 | −8.6 | −8.6 | −11.3 | −8.1 | −8.6 |
| ZINC17147426 | −7.8 | −8.8 | −8.2 | −10.9 | −8.4 | −8.2 |
| $QH_2$ | −7.9 | −8.5 | −8.2 | −9.0 | −8.5 | −8.3 |

Tunneling calculations were performed as described in Hayashi and Stuchebrukhov (2010) *Proc. Natl. Acad. Sci.* 107:19157; and Hagras and Stuchebrukhov (2015) *J. Phys. Chem. B.* 119:7712. The initial guess molecular orbitals (MOs) were generated using unrestricted Broken-Symmetry (BS) B3LYP method of Gaussian 09 package (Frish et al. (2009) Gaussian 09), employing ZINDO basis set for valence electrons and pseudo-potentials for core electrons.

The pruned systems were partitioned into donor, bridge, and acceptor(s) fragments of different charges and spin multiplicities, and consequently the tunneling electron was localized either on the donor or the acceptor site. The computed initial-guess MOs were then utilized in a subsequent BS-ZINDO calculation to obtain the corresponding BS donor and acceptor diabatic ground states, $$|\Psi_D\rangle = |\varphi_{1,\sigma}^D, \ldots, \varphi_{N,\sigma}^D\rangle, |\Psi_A\rangle = |\varphi_{1,\sigma}^A, \ldots, \varphi_{N,\sigma}^A\rangle.$$

The Hartree-Fock approximation assumed above, was validated in our recent study (Hagras and Stuchebrukhov (2015)). To simplify the tunneling calculation, the reduction from a fully multi-electronic picture to a one-electron approximation was accomplished by using bi-orthogonalization scheme of corresponding orbitals (Stuchebrukhov (2003) *J. Chem. Phys.* 118:7898; and Stuchebrukhov (2003) *Theor. Chem. Acc.* 110:291). The donor and acceptor orbitals with smallest overlap, and hence with most significant change during the tunneling transition, represent the tunneling pair of the one-electron approximation; the remaining corresponding (core) orbitals experience only relatively small change in the tunneling transition, with almost unit overlap, and contribute to the tunneling matrix element via the electronic Franck-Condon factor (Hagras and Stuchebrukhov (2015)). The transformed corresponding orbitals have the following form, $$|\Psi'_D\rangle = |\xi_{1,\alpha}^D, \ldots, \xi_{l,\alpha}^D, \xi_{1,\beta}^D, \ldots, \xi_{t,\beta}^D\rangle,$$

$$|\Psi'_A\rangle = |\xi_{1,\alpha}^A, \ldots, \xi_{l,\alpha}^A, \xi_{1,\beta}^A, \ldots, \xi_{t,\beta}^A\rangle$$

$$\langle \Psi'_D | \Psi'_A \rangle = \langle \xi_{i,\sigma}^D | \xi_{j,\beta}^A \rangle = \delta_{ij} s_i^\sigma$$

The product of the overlaps $s_i^\sigma$ of the core orbitals forms the electronic Franck-Condon factor $$\prod_i^l s_i^\alpha \prod_{j\neq t}^t s_j^\beta,$$

where we assume that the tunneling electron has a β-spin, and the tunneling orbital index "t" is the last one of the β-spin orbitals.

Since the ZINDO canonical MOs are represented in a basis set which is orthogonalized (using Löwdin-orthogonalization (Lowdin (1947) *Ark. Mat. Astr. Fys. A* 35:9) or other schemes) and therefore delocalized over many atoms, the localized atomic picture of inter-atomic tunneling currents in a tunneling transition is lost in this basis set. To conduct the tunneling current calculations, the atomic basis set localization needs therefore to be restored. By introducing the localized atomic basis set and the Mulliken type coarse-graining of the tunneling current, the tunneling transition flux is expressed in terms of the interatomic currents, which (approximately) has the following form (Stuchebrukhov (1998) *J. Chem. Phys.* 108:8510):

$$J_{ab} = \prod_i s_i^\alpha \prod_{j\neq t} s_j^\beta \sum_{\nu\in a}\sum_{\mu\in b}(H_{\nu\mu} - E_0 S_{\nu\mu})(\theta_{\mu\nu} - \theta_{\nu\mu})$$

Here ν and μ are the atomic orbitals of atoms a and b; $\theta_{\nu\mu} = A_\nu D_\mu$ where $D_\mu$ and $A_\nu$ are the expansion coefficients of the donor and acceptor tunneling orbitals, respectively; $H_{\nu\mu}$ and $S_{\nu\mu}$ are core Hamiltonian and overlap matrix, and $E_0$ is a tunneling orbital energy defined by, $$E_0 = \sum_{\lambda,\rho} D_\lambda F_{\lambda\rho} D_\rho = \sum_{\lambda,\rho} A_\lambda F_{\lambda\rho} A_\rho$$

where $F_{\mu\rho}$ is the reduced Fock matrix. The second equality in the above equation corresponds to the resonance of the donor and acceptor energies at the transition state of electron transfer reaction; in practice, the resonance is achieved by applying a static electric field mimicking the action of the polar environment and solvation effects.

The equation below shows that the inter-atomic currents are primarily determined by the overlap of the tails of the two tunneling orbitals. The electronic Franck-Condon factor $$\left(\prod_i s_i^\alpha \prod_{j\neq t} s_j^\beta\right)$$

contributes as a uniform scaling factor for all inter-atomic currents. The total atomic current through a given atom a, $$J_a^{tot} \equiv \frac{1}{2}\sum_b |J_{a,b}|,$$

is proportional to the probability that the tunneling electron is passing through this atom; as such, it provides a convenient way of identifying atoms that constitute the tunneling pathways. The tunneling matrix element that determines the rate of Electron Transfer (ET) is calculated as the total flux across the dividing surface between the donor and acceptor redox complexes (the flux theorem; Stuchebrukhov (2001) *Adv. Chem. Phys.* 118:1), $$T_{DA} = -\hbar \sum_{a\in S}\sum_{b\notin S} J_{ab}.$$

Figure 6:
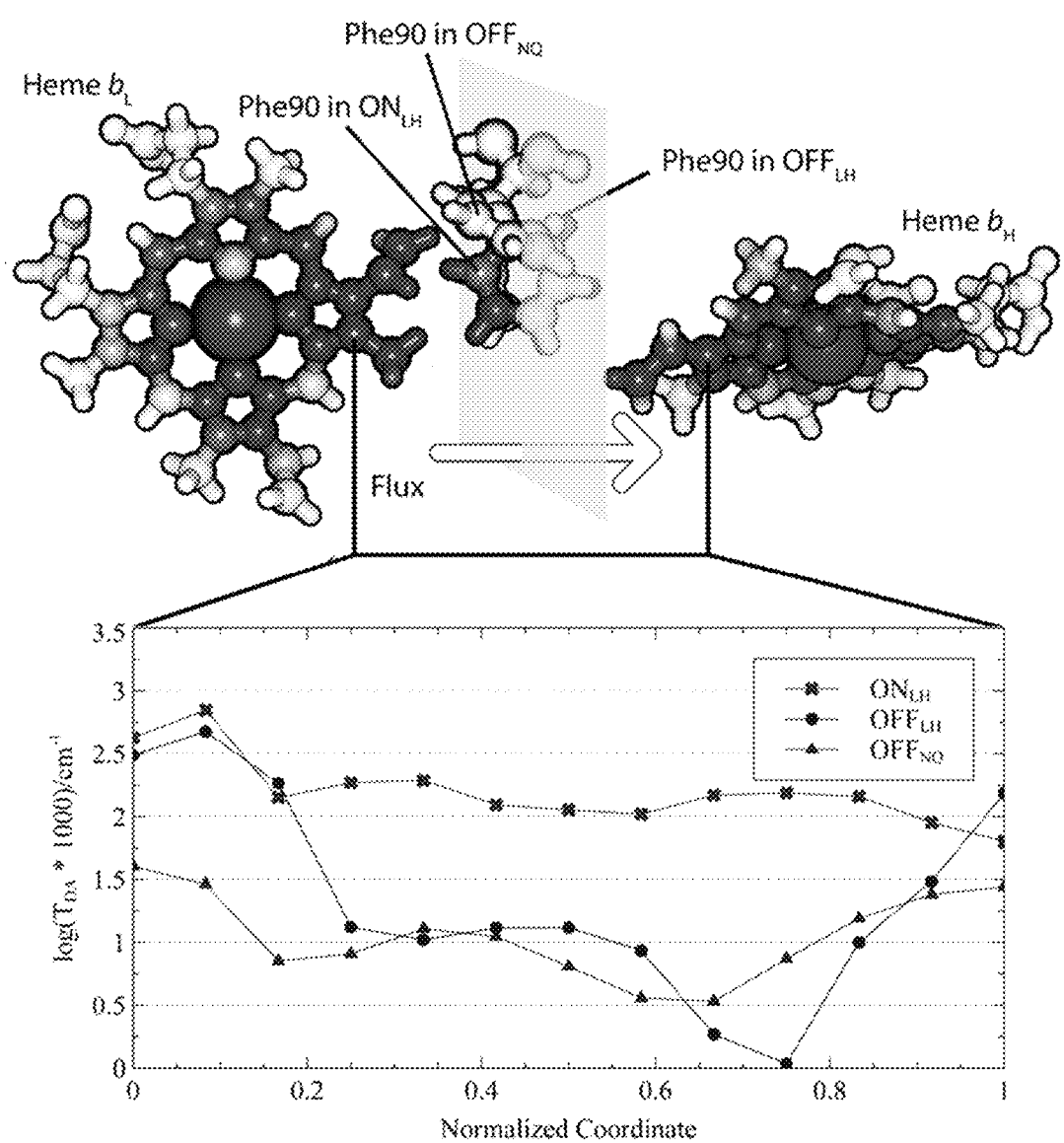
FIG. 6 illustrates electron tunneling flux through a dividing surface in heme $b_L$→heme $b_H$ redox system at three different Phe90 conformations ($ON_{LH}$, $OFF_{LH}$ and $OFF_{NQ}$). The flux plot shows the edge-to-edge tunneling flux at the different conformations plotted as $\log_{10}$ of the flux (adjusted by multiplying by 10) against the normalized coordinate.

Here, the summation of interatomic tunneling currents between atoms 'a' on one side, denoted as 'S' side, of the dividing surface and atoms 'b' on the other side (Stuchebrukhov (1996) *J. Chem. Phys.* 104:8424). The inter-atomic tunneling currents provide an internal assessment of the quality of calculation as a measure of conservation of the total tunneling flux between the donor and acceptor redox centers. An example is shown in FIG. 6 for a model heme $b_L \rightarrow E$ heme $b_H$ system with Phe90 in the ON conformation. The flux is approximately conserved along the whole tunneling pathway especially in the middle part, between donor and acceptor, as it should; to account for small variations, we compute the tunneling matrix element as an average over the middle region. All the studied systems behave in a similar manner. The value of the tunneling flux was taken as a measure of electron transfer rate in the analysis of different ligand-bound variants of $bc_1$ complex.

Figure 7:
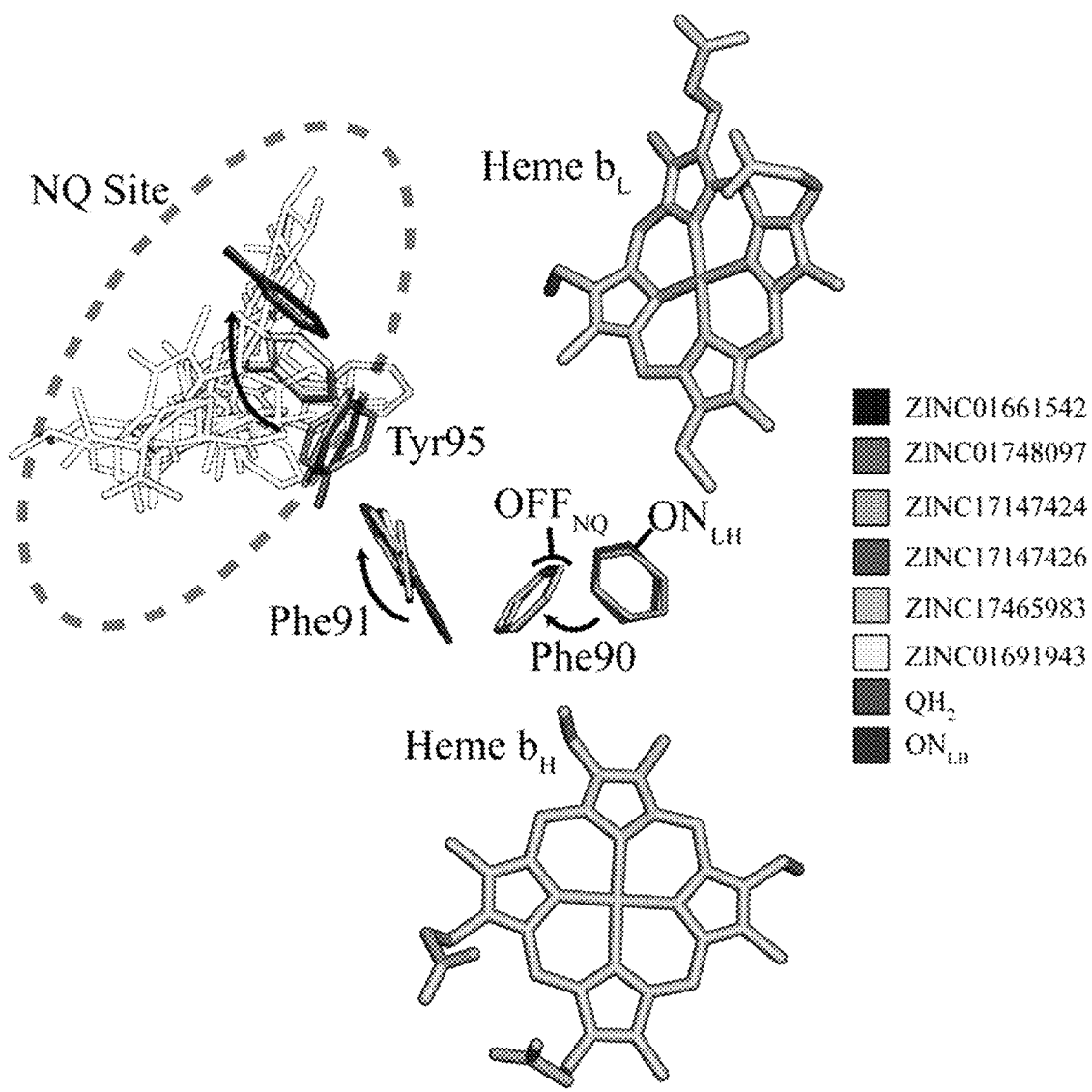
FIG. 7 illustrates docking of the selected ligands of FIG. 5 at NQ site. Different conformations of the flexible residues including the internal switch Phe90 residue are shown. The arrows signify the change from native $ON_{LH}$ conformation to the new ones.
Figure 8:
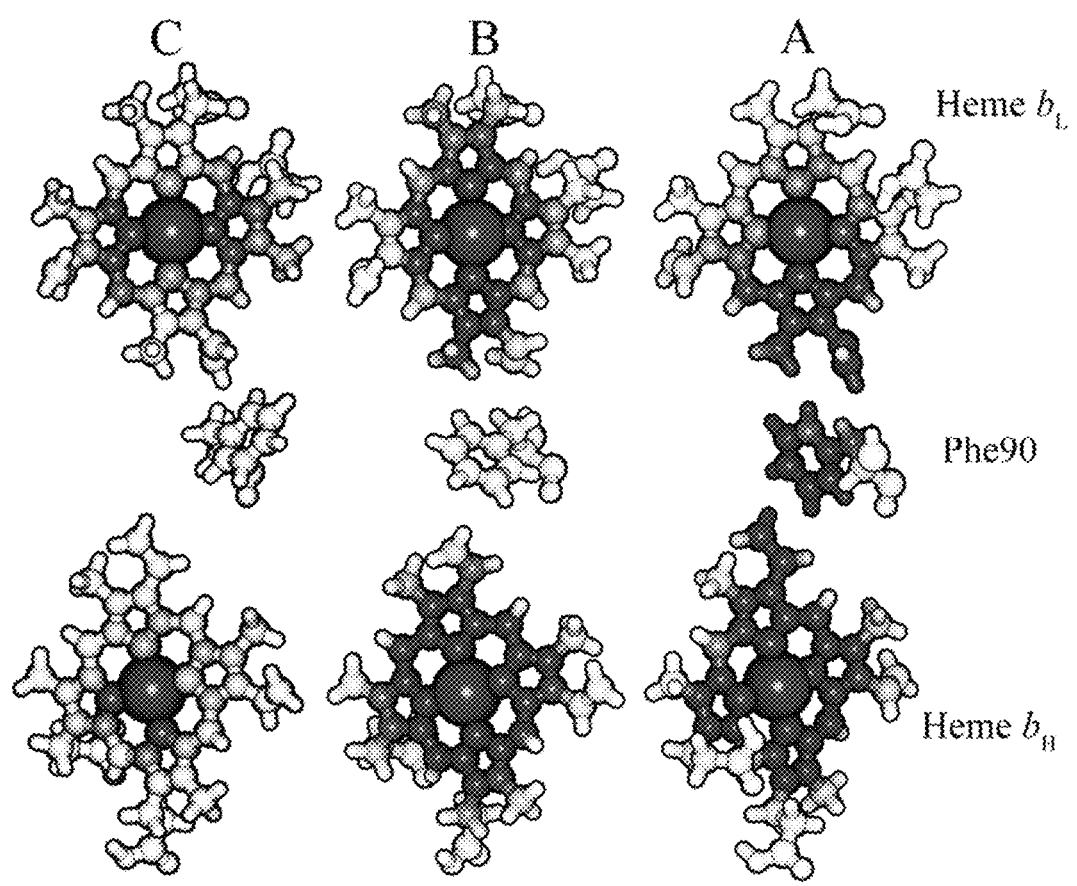
FIG. 8 illustrates calculated electron tunneling flux densities between heme $b_L$ and heme $b_H$ in two X-ray $bc_1$ crystal structures (PDB 1NTZ in A and C and 1NTK in B). Intensity of darkness corresponds to probability of a tunneling electron being on a given atom. A. residue Phe90 exists in $ON_{LH}$ conformation. B. residue Phe90 exists in $OFF_{LH}$ conformation. C. residue Phe90 exits in $OFF_{NQ}$ conformation.

As displayed in FIG. 7, the binding of the 6 candidate ligands from Example 1 at the NQ-site induces a series of conformational changes. Tyr95 undergoes moderate-to-substantial conformational changes that induce (along with a strong aromatic interaction due to the docked ligand) a conformational change of Phe91 residue, which ultimately attract the internal switch Phe90 residue from the intra-heme b region to OFF position. In short, compared to the natural $ON_{LH}$ conformation (which is attained by binding of $QH_2$ molecule at Q° site shown in FIG. 7), upon binding of 6 candidate ligands at the NQ-site, Phe90 residue swings away by a torsion angle of 76.31° and clusters at a conformation which we designate as $OFF_{NQ}$ (torsion angle equals 9.77° compared to $ON_{LH}$ with a torsion angle of 86.08°), as indicated in FIG. 7. As shown in FIG. 8, in $OFF_{NQ}$ conformation the electron tunneling flux is dramatically diminished, compared with the native $ON_{LH}$ conformation, which is an indication of significantly reduced electron transfer rate between heme $b_L$ and heme $b_H$.

Example 2. Molecular Dynamic Simulations

Molecular dynamics (MD) simulations of the five discovered ligands (excluding the isomer ZINC17147426) bound to ligand-free $bc_1$ structure (PDB ID: 1BE3) were conducted in order to verify the binding affinities of those ligands to NQ-site and in addition to confirm the proposed induced $OFF_{NQ}$ conformational change of the internal switch Phe90 residue. As shown in Table 2 the binding energies of the different ligands vary significantly in contrast to the results obtained above in the docking simulations (Table 1). Ligands ZINC01691943 and ZINC01748097 show the lowest stable binding energies while ligands ZINC01661542 and ZINC17465983 show comparably higher binding energies, with ligand ZINC17147424 having the highest binding energy of all.

Figure 10:
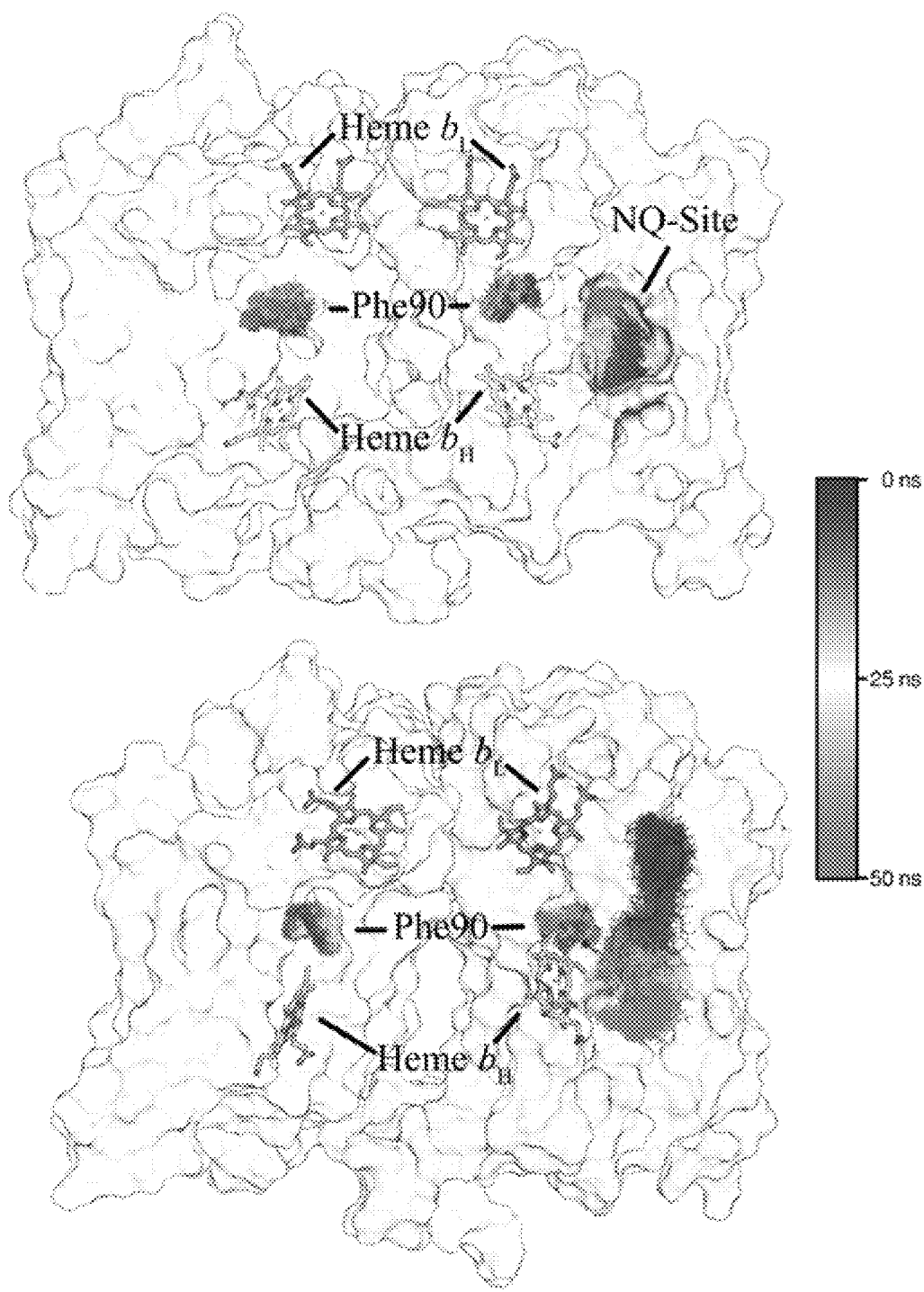
FIG. 10 is a visualization of 1000 snapshots of two different docked ligands (top, ZINC01691943 and bottom, ZINC17147424) at NQ-site in $bc_1$ structure (PDB: 1BE3) along with snapshots of the conformational changes of the Phe90 residue during the 50 ns MD run. The snapshots vary in darkness based on the simulation time-step.

Ultimately, ligand ZINC01691943 is the most promising one among the five ligands while ligand ZINC17147424 is the least promising one. Visualization of MD snapshots of the two ligands along with the Phe90 residue (and compare it to the other monomer Phe90 with a vacant $Q_o/Q_i/NQ$-sites) supports these conclusions. As shown in FIG. 10, ligand ZINC01691943 remains docked at NQ-site all over the simulation time and even binds tighter over time (as indicated by drakness gradient). In addition, it displaces the Phe90 residue away from the intra-heme b region as compared to the other monomer Phe90 residue. On the other hand, ligand ZINC17147424 unbinds from NQ-site and leads to undesired conformational changes of Phe90 residue.

Example 3. Continued in Silico Screening of Ligand Binding Motifs

Figure 11:
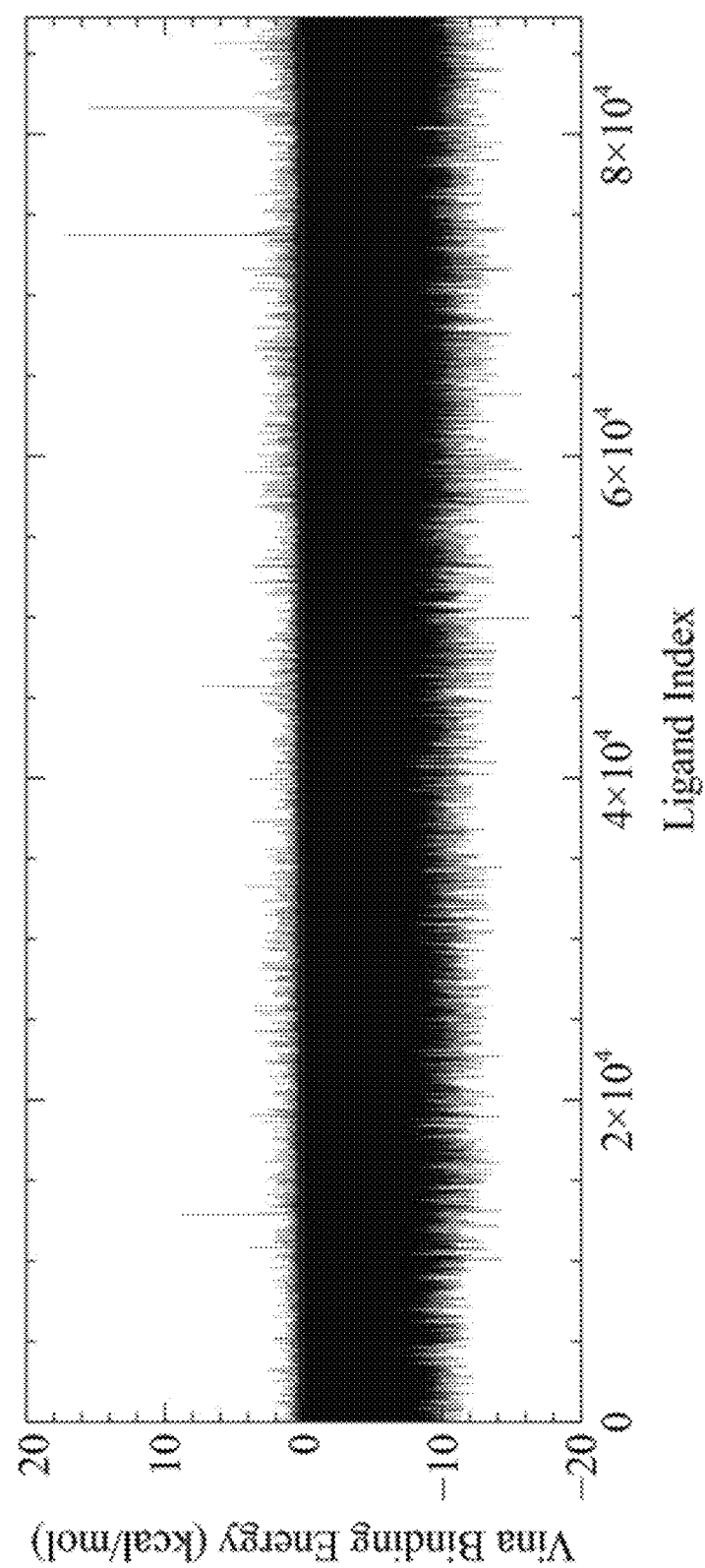
FIG. 11 is a graph of Autodock Vina docking results of the ZINC database ligands set at the NQ-site using fixed residues against flexible residues. The positive differences of the binding energies are plotted at the top as positive values.

All currently-available 87,257 molecules was retrieved from the ZINC database. The subset was processed further by AutoDockTools utility (Raccoon) to convert from Sybyl mol2 format to Autodock PDBQT format. A series of virtual screening calculations were carried out of the docking of the ligands with the NQ-binding site using PyRx0.9.2 utilizing both Lamarckian Genetic Algorithm (LG) search method in Autodock 4.2 and Autodock Vina 4.2 advanced gradient optimization search method. Default settings were used for both Autodock Vina and LG search methods. To account for flexibility of the NQ-binding site and the different possible conformations of the Phe90 residue, we performed the docking calculation at both fixed and flexible residues (Phe90, Phe91, Ile92, Leu94 and Tyr95) modes as shown in FIG. 11.

TABLE 2

Binding energy averaged components for the five ligands at NQ-site during the MD simulation trajectory (in units of kcal/mol).

| | $E_{elec}$ | $E_{vdw}$ | $E_{polar}$ | $E_{SASA}$ | $E_{bind}$ |
|---|---|---|---|---|---|
| ZINC01661542 | −36.47 (1.36)* | 0.65 (0.25) | 10.36 (0.88) | −3.99 (0.11) | −29.45 (0.83) |
| ZINC01691943 | −30.52 (0.56) | −56.19 (4.96) | 17.91 (1.86) | −3.38 (0.26) | −72.17 (6.24) |
| ZINC01748097 | −35.57 (1.22) | 2.44 (3.69) | −9.16 (0.51) | −4.49 (0.23) | −46.77 (4.08) |
| ZINC17147424 | −21.22 (1.66) | −8.70 (3.70) | 14.22 (2.37) | −2.81 (0.18) | −18.50 (3.82) |
| ZINC17465983 | −29.44 (4.77) | −3.38 (1.94) | 13.34 (0.69) | −3.57 (0.16) | −23.05 (6.17) |

*The values in parenthesis indicate the variation estimate of the corresponding quantity along the MD trajectory.

Figure 9A:
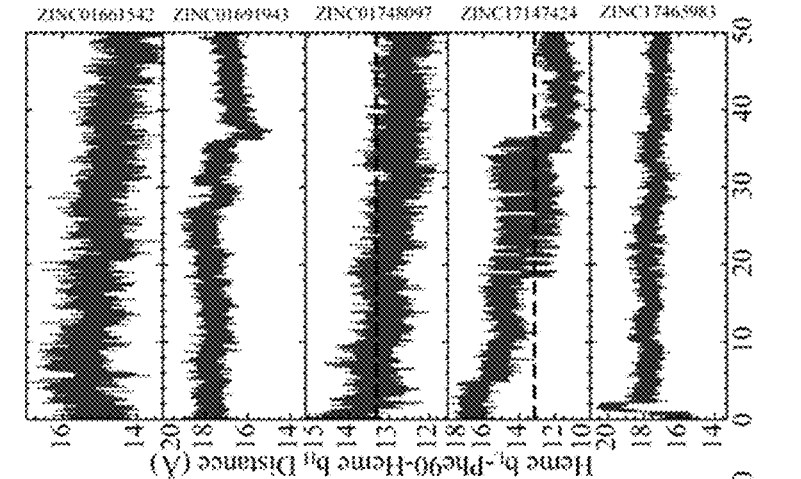
FIGS. 9A-9C present molecular dynamics simulation results of the five discovered ligands of FIG. 5 docked in pre-energy minimized $bc_1$ complex (PDB: 1BE3).
Figure 9B:
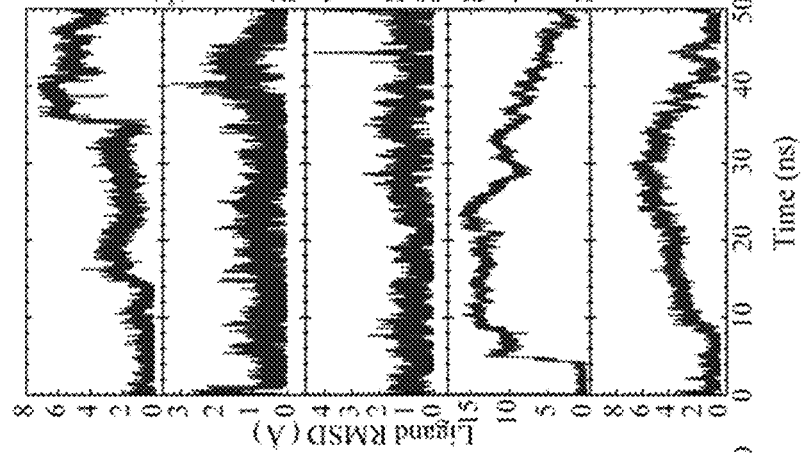
Figure 9C:
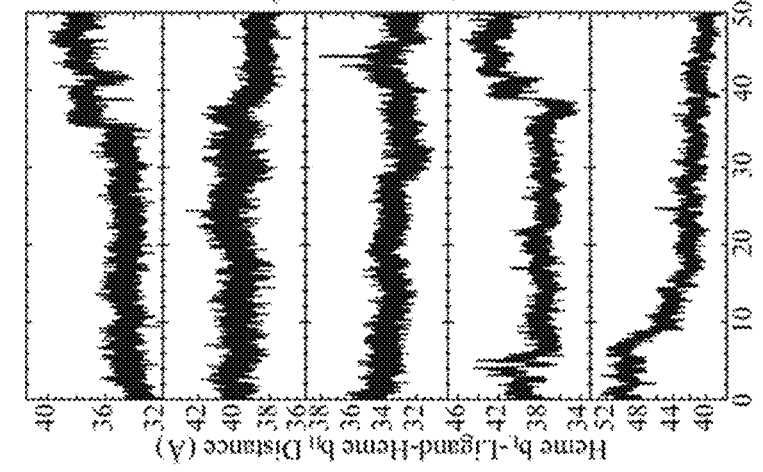

Analysis of the MD simulations trajectories for the different ligands further validates their binding mode and proposed influence on Phe90 conformation. As shown in Figure FIG. 9A, ligands ZINC01691943 and ZINC01748097 remain bound to NQ-site during the whole 50 ns simulation time and even get closer to heme $b_L$-heme$b_H$ system. Those two ligands show high magnitude of stability as indicated by their minimal RMSD during the simulation time (FIG. 9B). Nevertheless, only ligand ZINC01691943 induces the desired conformational changes of Phe90 as indicated in FIG. 9C where the total computed distance of the displaced Phe90 is greater than that found in Q-bound $bc_1$ structure (PDB: 1NTZ, distance=13.3 Å) along the whole simulation time. Of the next two ligands ZINC01661542 and ZINC17465983, only ligand ZINC17465983 remains tightly-bound and produces the desired conformational changes of Phe90 residue. Finally, as expected for having the highest binding energy, ligand ZINC17147424 undocks from NQ-site, shows the highest RMSD at NQ-site which decreases as it leaves the site and also fails to keep the desired conformational changes of Phe90 residue.

Figure 12:
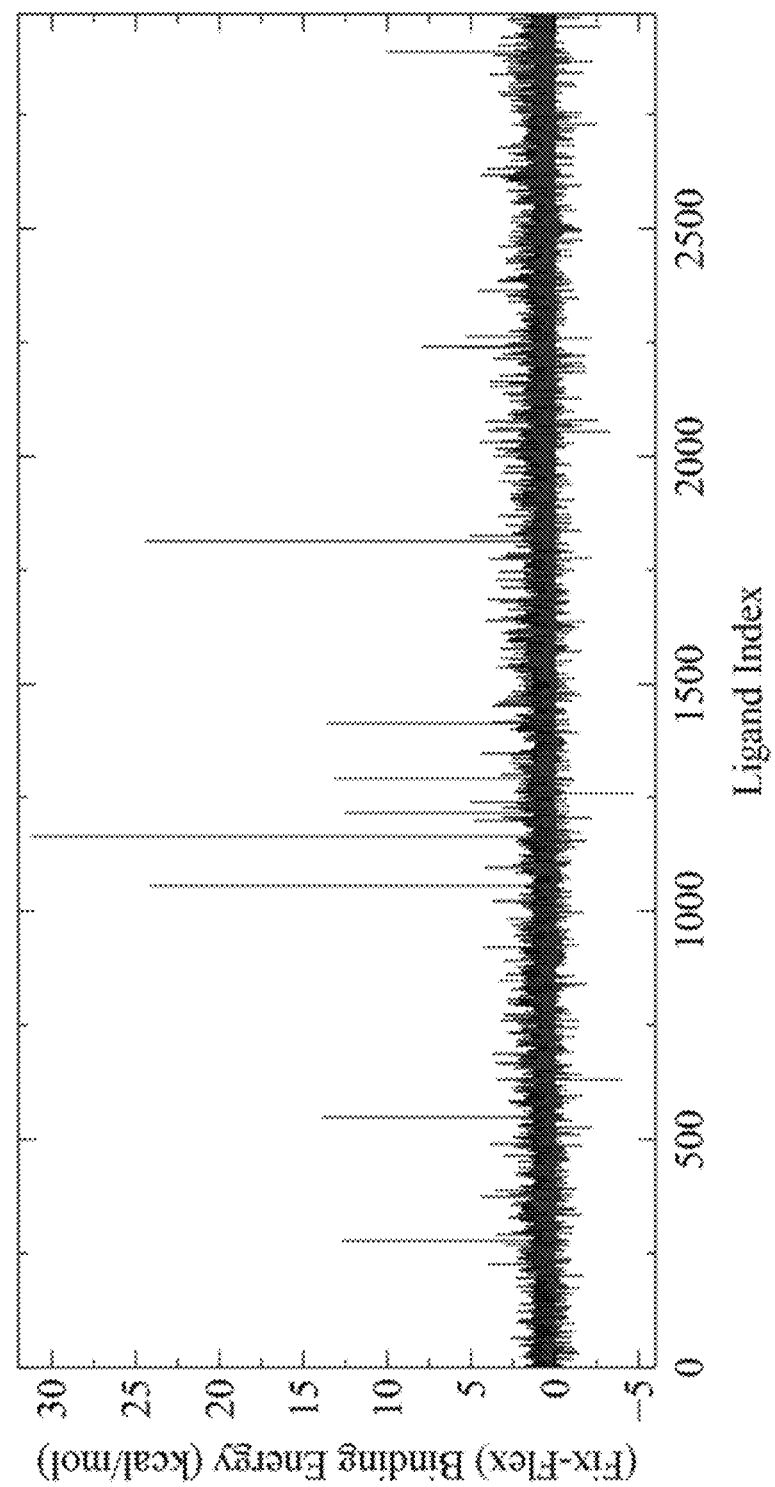
FIG. 12 is a graph of Fix-Flex binding energies at NQ site for the selected 2,969 ligands using Vina and LG search algorithms.

From the data in FIG. 11, only 2,969 ligands show a preferential binding by at least 1 kcal/mol at NQ-site in the flexible-residues docking mode compared to the fixed mode using Autodock Vina docking algorithm. Those 2,969 ligands were challenged in a subsequent docking calculation at NQ-site using the Autodock Lamarckian Genetic (LG) algorithm as shown in FIG. 12. Only 353 ligands passed the second screening with at least 1 kcal/mol in the flexible mode compared to the fixed mode. Additionally those ligands were selected that have lower flexible-mode binding affinity to NQ-site compared to $QH_2$ molecule (which has binding energy for NQ-site equals to −8.75 kcal/mol) in both docking algorithms.

Figure 13:
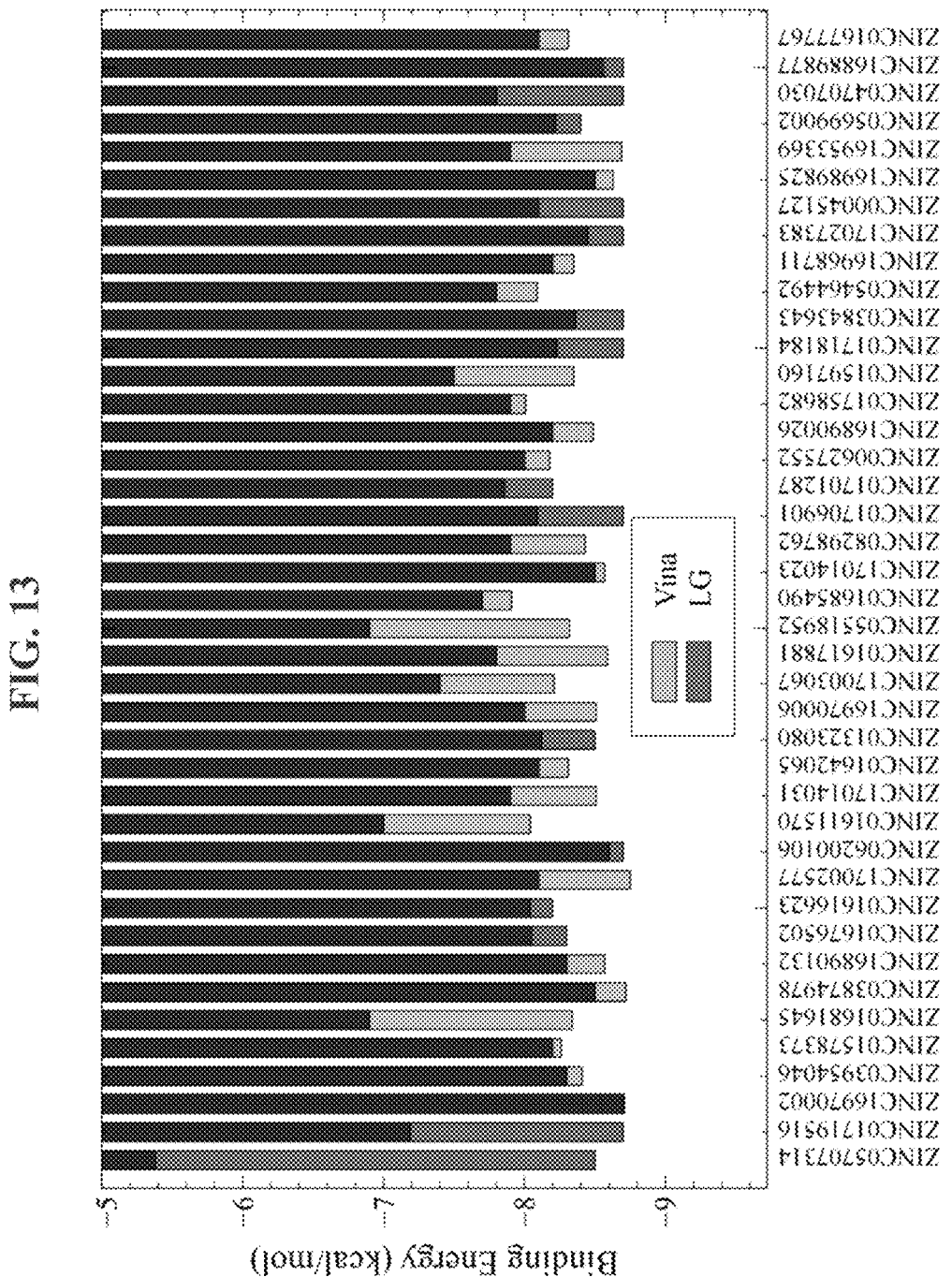
FIG. 13 is a graph of docking results at $Q_o$ site (1NTZ in PDB) of the selected 41 ligands from FIG. 12 using Vina (light grey bars) and LG (dark grey bars) search algorithms. Black bars represent the overlap between Vina and LG corresponding bars.

In addition to the above criteria, we further restricted the ligand class search such that the candidate ligands would not compete with $QH_2$ molecule for binding at $Q_o$ site. Further docking analysis of the resultant 353 ligands into the active $Q_o$ site (as it exists in PDB 1NTZ) reduced the number of ligands down to 41 candidates. As shown in FIG. 13, those 41 candidate ligands exhibit binding energy higher than −8.8 kcal/mol in both docking methods and hence would bind preferentially at NQ-site, but not at $Q_o$ site as compared to $QH_2$ molecule.

Investigating the chemical structures of those 41 ligands reveals that all share binding motifs composed of cyclic rings but differ in the number of fused, directly or indirectly-connected rings. Therefore we classify those ligands under 4 different classes based on the number of rings involved in the binding motifs and whether they are fused or directly/indirectly bonded as listed in Table 3 and shown in FIG. 14.

TABLE 3

Different binding motif classes of the NQ-site ligands and their corresponding ligand IDs.

| Class | Ligand Binding Motif | Ligand ID |
|---|---|---|
| I | 2 fused rings | ZINC00045127, ZINC01323080, ZINC01677767, ZINC01701287, ZINC01706901, ZINC01758682 |
| II | 2 directly- or indirectly-bonded rings | ZINC00627552, ZINC01681645, ZINC05518952 |
| III | 3 fused or bonded rings | ZINC01611570, ZINC01685490, ZINC01718184, ZINC05464492, ZINC05699002, ZINC16889877, ZINC16968711 |
| IV | 4 or more fused or bonded rings | ZINC01578373, ZINC03843643, ZINC03874978, ZINC03954046, ZINC04707030, ZINC06200106, ZINC08298762, ZINC16890026, ZINC16890132, ZINC16953369, ZINC16970002, ZINC16970006, ZINC16989825, ZINC17002577, ZINC17003067, ZINC17014023, ZINC17014031, ZINC01597160, ZINC01616623, ZINC01617881, ZINC01642065, ZINC01676502, ZINC01719516, ZINC05707314, ZINC17027383 |

In the molecular dynamics (MD) simulation study of Example 2, we discovered that a ligand binding motif at NQ-SITE of two fused aromatic rings (such as the indole of ZINC01691943) can show lower binding energy (−72.17±6.24 kcal/mol) than that observed with a higher or lower number of fused rings. In addition, we found that the conjugated aromaticity of the binding motif can contribute to lower binding energy (as seen with ZINC17465983 compared to ZINC01661542, where both have binding motif of three fused rings while ZINC01661542 lacks the conjugated system). Finally, we believe that the aromatic character of the binding motif can improve the switching off of the internal switch (LH, Phe90) through aromatic-aromatic interactions which induce the required conformational changes.

The Class I (such as ZINC00045127) ligands present natural extensions, in different directions, to the binding motif of two fused aromatic rings (benzene ring fused with pyrrole ring forming indole compound as shown in ligand ZINC01691943). The first extension is that the ligands not only furnish two binding motifs bonded covalently (as in ligand ZINC17465983) or through a longer intervening chain (two covalent bonds, as in ligand ZINC01691943) but also they can be spiro-fused (share one atom) as shown in ligand ZINC00045127. Moreover the ligands ZINC01323080, ZINC01677767, ZINC01701287, ZINC01706901 and ZINC01758682 only have one binding motif. A further addition to the binding motif structure is seen in those ligands where the fused ring system is not an indole one but rather a tetralin system (benzene ring fused with cyclohexane ring) or even larger heterocyclic ring (1,4 diazepine ring) fused with a benzene ring. Another finding regarding class I ligands is that not all of them show a conjugated aromatic system, yet such conjugated aromaticity can impart higher binding affinity and stronger aromatic-aromatic interaction inducing the desired conformational changes down to the internal switch Phe90 residue.

Class II ligands present a dramatic extension to class I ligands in that class II ligands show that the ligand binding motif can be composed of two covalently-bonded rings instead of two fused rings. Because in such systems the distance between the two ring edges is very close to that of three fused-rings system, the conjugated aromaticity can ensure proper binding and desired conformational induction. Otherwise, as we experienced in the MD simulations of Example 1, the system lacking conjugated aromaticity (ZINC01661542) unbinds from the NQ-site much earlier compared to the system with conjugated aromaticity (ZINC17465983).

Class III ligands can represent an upper limit of the ligand size (three-fused rings) that can fit in NQ-site and remain bound provided that they have conjugated aromatic character. Based on the MD simulations of Example 2, class IV ligands can be more prone to leak out of NQ-site.

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method of inhibiting respiratory complex III in a cell, comprising:
contacting the cell with a compound having a structure selected from the group consisting of:

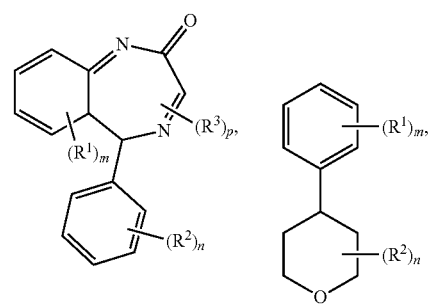

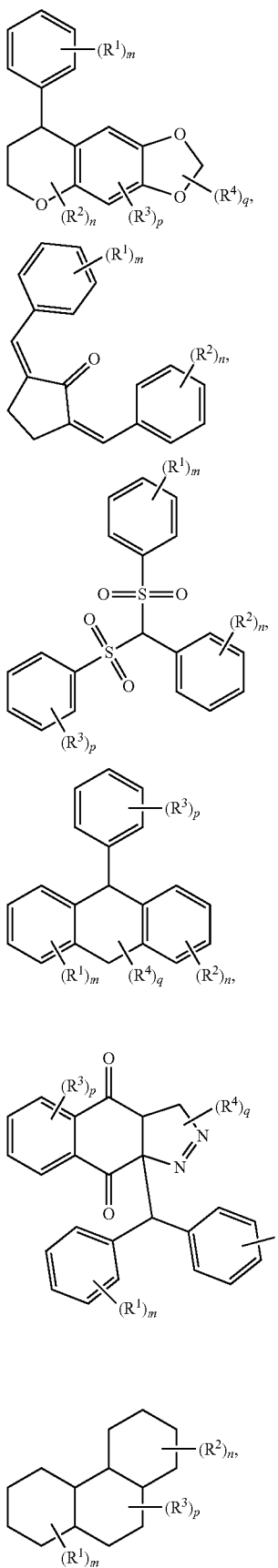

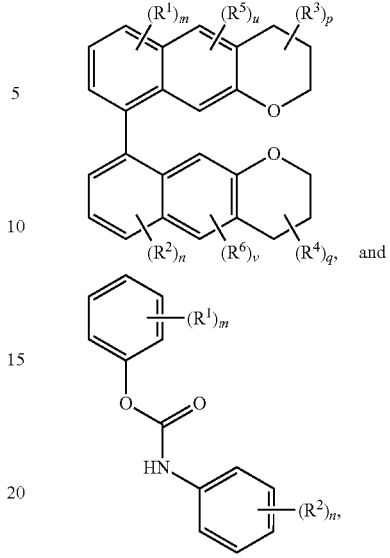

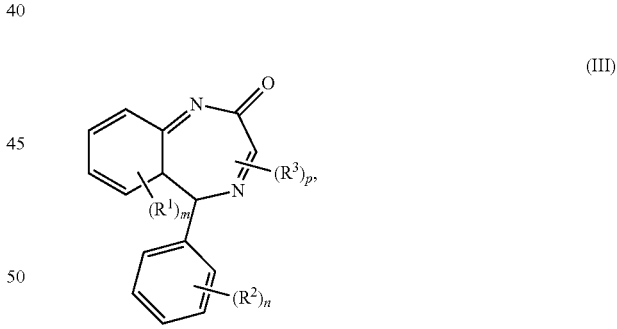

wherein
each $R^1$, $R^2$, $R^3$, $R^4$, $R^5$, and $R^6$ is independently selected from the group consisting of hydrogen, $C_{1-6}$ alkyl, $C_{1-6}$ alkylhydroxy, $C_{1-6}$ haloalkyl, $C_{1-6}$ alkoxy, $C_{1-6}$ haloalkoxy, $C_{6-12}$ aryl, halogen, hydroxyl, oxide, —CN, —NH$_2$, —NO$_2$, and —C(O)—C$_{1-6}$ alkyl, and —C(O)O$^-$;
the subscripts m and n are each independently integers from 0 to 5;
the subscript p is an integer from 0 to 4; and
the subscripts q, u, and v are each independently integers from 0 to 2;
such that the compound binds to respiratory complex III, thereby inhibiting respiratory complex III.

2. The method of claim 1, wherein the compound has the structure of Formula III:

(III)

wherein
each $R^1$ is independently selected from the group consisting of hydrogen, $C_{1-6}$ alkyl, $C_{1-6}$ alkoxy, halogen, hydroxyl, —NO$_2$, and —C(O)—C$_{1-6}$ alkyl;
each $R^2$ is independently selected from the group consisting of hydrogen, $C_{1-6}$ alkyl, $C_{1-6}$ alkoxy, $C_{6-12}$ aryl, hydroxyl, —CN, —NH$_2$, —C(O)O—C$_{1-6}$ alkyl, and —C(O)O$^-$,
each $R^3$ is independently selected from the group consisting of hydrogen, $C_{1-6}$ alkyl, $C_{1-6}$ alkoxy, and oxide;
the subscripts m and n are each independently integers from 0 to 5; and
the subscript p is an integer from 0 to 4.

3. The method of claim 1, wherein the compound has the structure of Formula IV:

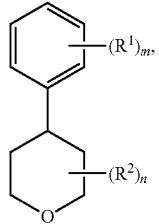

(IV)

wherein
- each $R^1$ is independently selected from the group consisting of hydrogen, $C_{1-6}$ alkyl, $C_{1-6}$ alkoxy, halogen, hydroxyl, —$NO_2$, and —C(O)—$C_{1-6}$ alkyl;
- each $R^2$ is independently selected from the group consisting of hydrogen, $C_{1-6}$ alkyl, $C_{1-6}$ alkoxy, $C_{6-12}$ aryl, hydroxyl, —CN, —$NH_2$, —C(O)O—$C_{1-6}$ alkyl, and —C(O)O$^-$, and
- the subscripts m and n are each independently integers from 0 to 5.

4. The method of claim 1, wherein the compound has the structure of Formula V:

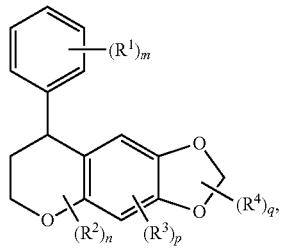

(V)

wherein
- each $R^1$ is independently selected from the group consisting of hydrogen, $C_{1-6}$ alkyl, $C_{1-6}$ alkoxy, halogen, hydroxyl, —$NO_2$, and —C(O)—$C_{1-6}$ alkyl;
- each $R^2$ is independently selected from the group consisting of hydrogen, $C_{1-6}$ alkyl, $C_{1-6}$ alkoxy, $C_{6-12}$ aryl, hydroxyl, —CN, —$NH_2$, —C(O)O—$C_{1-6}$ alkyl, and —C(O)O$^-$,
- each $R^3$ is independently selected from the group consisting of hydrogen, $C_{1-6}$ alkyl, $C_{1-6}$ alkoxy, and oxide;
- each $R^4$ is independently selected from the group consisting of hydrogen and $C_{1-6}$ alkyl;
- the subscripts m and n are each independently integers from 0 to 5;
- the subscript p is an integer from 0 to 4; and
- the subscript q is an integer from 0 to 2.

5. The method of claim 1, wherein the compound has the structure of Formula VI:

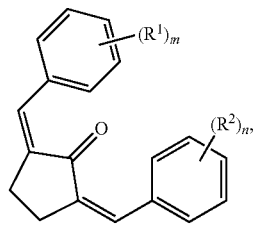

(VI)

wherein
- each $R^1$ is independently selected from the group consisting of hydrogen, $C_{1-6}$ alkyl, $C_{1-6}$ alkoxy, halogen, hydroxyl, —$NO_2$, and —C(O)—$C_{1-6}$ alkyl;
- each $R^2$ is independently selected from the group consisting of hydrogen, $C_{1-6}$ alkyl, $C_{1-6}$ alkoxy, $C_{6-12}$ aryl, hydroxyl, —CN, —$NH_2$, —C(O)O—$C_{1-6}$ alkyl, and —C(O)O$^-$, and
- the subscripts m and n are each independently integers from 0 to 5.

6. The method of claim 1, wherein the compound has the structure of Formula VII:

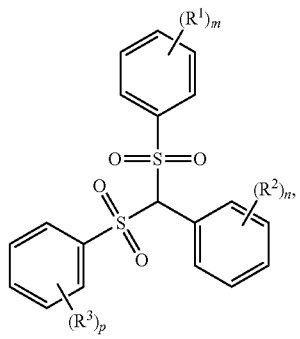

(VII)

wherein
- each $R^1$ is independently selected from the group consisting of hydrogen, $C_{1-6}$ alkyl, $C_{1-6}$ alkoxy, halogen, hydroxyl, —$NO_2$, and —C(O)—$C_{1-6}$ alkyl;
- each $R^2$ is independently selected from the group consisting of hydrogen, $C_{1-6}$ alkyl, $C_{1-6}$ alkoxy, $C_{6-12}$ aryl, hydroxyl, —CN, —$NH_2$, —C(O)O—$C_{1-6}$ alkyl, and —C(O)O$^-$,
- each $R^3$ is independently selected from the group consisting of hydrogen, $C_{1-6}$ alkyl, $C_{1-6}$ alkoxy, and oxide;
- the subscripts m and n are each independently integers from 0 to 5; and
- the subscript p is an integer from 0 to 4.

7. The method of claim 1, wherein the compound has the structure of Formula VIII:

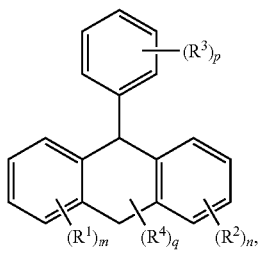

(VIII)

wherein
- each $R^1$ is independently selected from the group consisting of hydrogen, $C_{1-6}$ alkyl, $C_{1-6}$ alkoxy, halogen, hydroxyl, —$NO_2$, and —C(O)—$C_{1-6}$ alkyl;
- each $R^2$ is independently selected from the group consisting of hydrogen, $C_{1-6}$ alkyl, $C_{1-6}$ alkoxy, $C_{6-12}$ aryl, hydroxyl, —CN, —$NH_2$, —C(O)O—$C_{1-6}$ alkyl, and —C(O)O⁻,
- each $R^3$ is independently selected from the group consisting of hydrogen, $C_{1-6}$ alkyl, $C_{1-6}$ alkoxy, and oxide;
- each $R^4$ is independently selected from the group consisting of hydrogen and $C_{1-6}$ alkyl;
- the subscripts m and n are each independently integers from 0 to 5;
- the subscript p is an integer from 0 to 4; and
- the subscript q is an integer from 0 to 2.

8. The method of claim 1, wherein the compound has the structure of Formula IX:

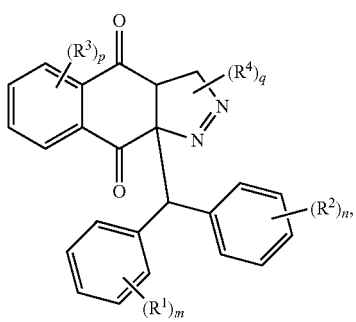

(IX)

wherein
- each $R^1$ is independently selected from the group consisting of hydrogen, $C_{1-6}$ alkyl, $C_{1-6}$ alkoxy, halogen, hydroxyl, —$NO_2$, and —C(O)—$C_{1-6}$ alkyl;
- each $R^2$ is independently selected from the group consisting of hydrogen, $C_{1-6}$ alkyl, $C_{1-6}$ alkoxy, $C_{6-12}$ aryl, hydroxyl, —CN, —$NH_2$, —C(O)O—$C_{1-6}$ alkyl, and —C(O)O⁻,
- each $R^3$ is independently selected from the group consisting of hydrogen, $C_{1-6}$ alkyl, $C_{1-6}$ alkoxy, and oxide;
- each $R^4$ is independently selected from the group consisting of hydrogen and $C_{1-6}$ alkyl;
- the subscripts m and n are each independently integers from 0 to 5;
- the subscript p is an integer from 0 to 4; and
- the subscript q is an integer from 0 to 2.

9. The method of claim 1, wherein the compound has the structure of Formula X:

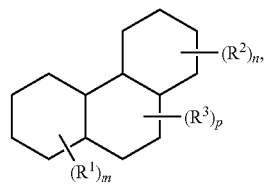

(X)

wherein
- each $R^1$ is independently selected from the group consisting of hydrogen, $C_{1-6}$ alkyl, $C_{1-6}$ alkoxy, halogen, hydroxyl, —$NO_2$, and —C(O)—$C_{1-6}$ alkyl;
- each $R^2$ is independently selected from the group consisting of hydrogen, $C_{1-6}$ alkyl, $C_{1-6}$ alkoxy, $C_{6-12}$ aryl, hydroxyl, —CN, —$NH_2$, —C(O)O—$C_{1-6}$ alkyl, and —C(O)O⁻,
- each $R^3$ is independently selected from the group consisting of hydrogen, $C_{1-6}$ alkyl, $C_{1-6}$ alkoxy, and oxide;
- the subscripts m and n are each independently integers from 0 to 5; and
- the subscript p is an integer from 0 to 4.

10. The method of claim 1, wherein the compound has the structure of Formula XII:

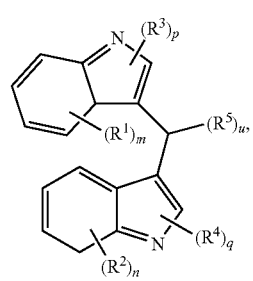

(XII)

wherein
- each $R^1$ is independently selected from the group consisting of hydrogen, $C_{1-6}$ alkyl, $C_{1-6}$ alkoxy, halogen, hydroxyl, —$NO_2$, and —C(O)—$C_{1-6}$ alkyl;
- each $R^2$ is independently selected from the group consisting of hydrogen, $C_{1-6}$ alkyl, $C_{1-6}$ alkoxy, $C_{6-12}$ aryl, hydroxyl, —CN, —$NH_2$, —C(O)O—$C_{1-6}$ alkyl, and —C(O)O⁻,
- each $R^3$ is independently selected from the group consisting of hydrogen, $C_{1-6}$ alkyl, $C_{1-6}$ alkoxy, and oxide;
- each $R^4$ is independently selected from the group consisting of hydrogen and $C_{1-6}$ alkyl;
- each $R^5$ is independently selected from the group consisting of hydrogen, $C_{1-6}$ alkyl, hydroxyl, and C(O)O⁻;
- the subscripts m and n are each independently integers from 0 to 5;
- the subscript p is an integer from 0 to 4; and
- the subscripts q and u are each independently integers from 0 to 2.

11. The method of claim 1, wherein the compound has the structure of Formula XIII:

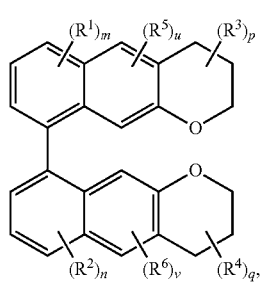
(XIII)

wherein
  each $R^1$ is independently selected from the group consisting of hydrogen, $C_{1-6}$ alkyl, $C_{1-6}$ alkoxy, halogen, hydroxyl, —$NO_2$, and —C(O)—$C_{1-6}$ alkyl;
  each $R^2$ is independently selected from the group consisting of hydrogen, $C_{1-6}$ alkyl, $C_{1-6}$ alkoxy, $C_{6-12}$ aryl, hydroxyl, —CN, —$NH_2$, —C(O)O—$C_{1-6}$ alkyl, and —C(O)O$^-$,
  each $R^3$ is independently selected from the group consisting of hydrogen, $C_{1-6}$ alkyl, $C_{1-6}$ alkoxy, and oxide;
  each $R^4$ is independently selected from the group consisting of hydrogen and $C_{1-6}$ alkyl;
  each $R^5$ is independently selected from the group consisting of hydrogen, $C_{1-6}$ alkyl, hydroxyl, and C(O)O$^-$;
  each $R^6$ is independently selected from the group consisting of hydrogen and hydroxyl;
  the subscripts m and n are each independently integers from 0 to 5;
  the subscript p is an integer from 0 to 4;
  the subscripts q, u, and v are each independently integers from 0 to 2; and
  the subscript w is an integer from 0 to 3.
12. The method of claim 1, wherein the compound has the structure of Formula XIV:

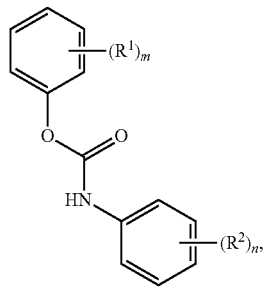
(XIV)

wherein
  each $R^1$ is independently selected from the group consisting of hydrogen, $C_{1-6}$ alkyl, $C_{1-6}$ alkoxy, halogen, hydroxyl, —$NO_2$, and —C(O)—$C_{1-6}$ alkyl;
  each $R^2$ is independently selected from the group consisting of hydrogen, $C_{1-6}$ alkyl, $C_{1-6}$ alkoxy, $C_{6-12}$ aryl, hydroxyl, —CN, —$NH_2$, —C(O)O—$C_{1-6}$ alkyl, and —C(O)O$^-$, and
  the subscripts m and n are each independently integers from 0 to 5.
13. The method of claim 1, wherein the compound is selected from group consisting of

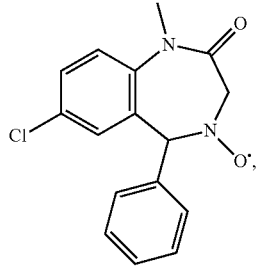

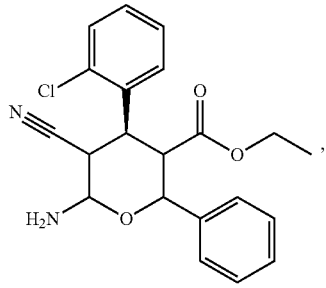

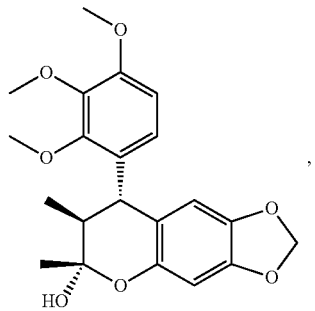

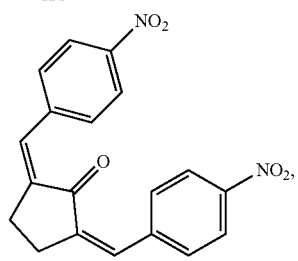

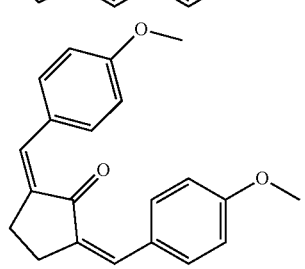

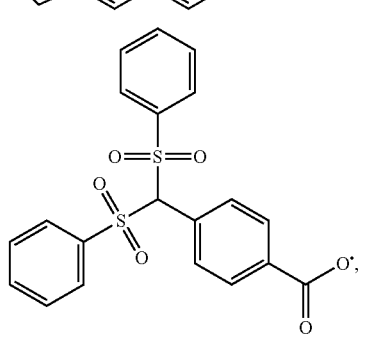

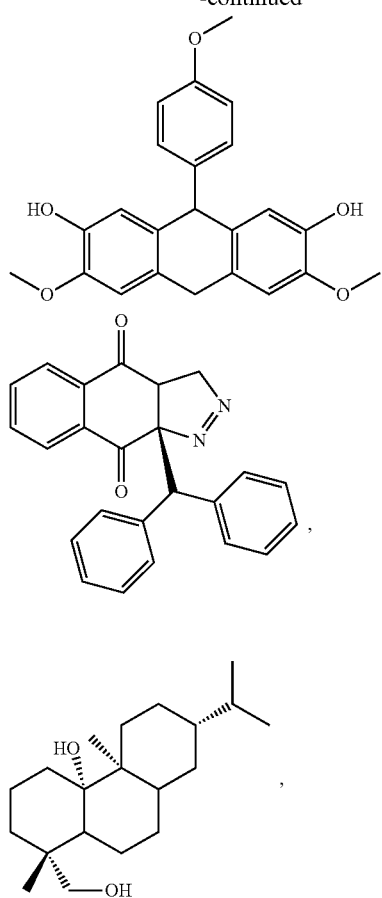
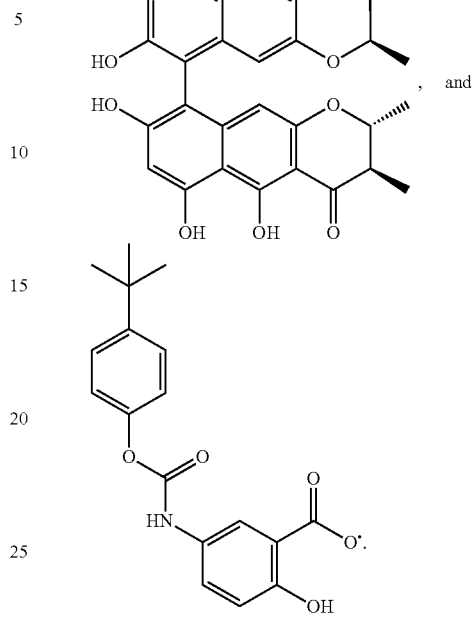
14. The method of claim 1, wherein the cell is a cancer cell.
15. The method of claim 14, wherein the cancer cell is in a subject.
16. The method of claim 15, further comprising administering to the subject an amount of the compound effective to inhibit respiratory complex III in the cancer cell.
* * * * *